US011208634B2

(12) United States Patent
Vallera

(10) Patent No.: US 11,208,634 B2
(45) Date of Patent: Dec. 28, 2021

(54) DEIMMUNIZED THERAPEUTIC COMPOSITIONS AND METHODS

(71) Applicant: Regents of the University of Minnesota, Minneapolis, MN (US)

(72) Inventor: Daniel Attilio Vallera, Richfield, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 64 days.

(21) Appl. No.: 15/764,047

(22) PCT Filed: Sep. 30, 2016

(86) PCT No.: PCT/US2016/054823
§ 371 (c)(1),
(2) Date: Mar. 28, 2018

(87) PCT Pub. No.: WO2017/059270
PCT Pub. Date: Apr. 6, 2017

(65) Prior Publication Data
US 2018/0273920 A1   Sep. 27, 2018

Related U.S. Application Data

(60) Provisional application No. 62/236,568, filed on Oct. 2, 2015.

(51) Int. Cl.
| | |
|---|---|
| *A61K 47/68* | (2017.01) |
| *C07K 14/34* | (2006.01) |
| *A61K 38/00* | (2006.01) |
| *C12N 9/10* | (2006.01) |
| *C07K 14/54* | (2006.01) |
| *C07K 14/485* | (2006.01) |
| *A61P 35/00* | (2006.01) |

(52) U.S. Cl.
CPC ........ *C12N 9/1077* (2013.01); *A61K 47/6829* (2017.08); *A61P 35/00* (2018.01); *C07K 14/34* (2013.01); *C07K 14/485* (2013.01); *C07K 14/5437* (2013.01); *C12Y 204/02036* (2013.01); *A61K 38/00* (2013.01); *C07K 2319/01* (2013.01); *C07K 2319/33* (2013.01); *C07K 2319/55* (2013.01); *C07K 2319/74* (2013.01)

(58) Field of Classification Search
None
See application file for complete search history.

(56) References Cited

U.S. PATENT DOCUMENTS

| | | | | |
|---|---|---|---|---|
| 2009/0010966 | A1* | 1/2009 | Davis | A61P 35/02 424/238.1 |
| 2012/0121614 | A1* | 5/2012 | Vallera | A61K 38/164 424/178.1 |
| 2016/0340394 | A1* | 11/2016 | Poma | C07K 16/286 |

FOREIGN PATENT DOCUMENTS

WO    WO 2016/187585    * 11/2016

OTHER PUBLICATIONS

Lazar et al. Mol. Cellular Biol. 8: 1247-1252, 1988.*
Cleton-Jansen et al. Mol. Gen. Genet. 229: 206-212, 1991.*
International Patent Application No. PCT/US2016/054823, filed Sep. 30, 2016, International Search Report / Written Opinion dated Dec. 15, 2016; 14 pages.
International Patent Application No. PCT/US2016/054823, filed Sep. 30, 2016, International Preliminary Report on Patentability dated Apr. 12, 2018; 8 pages.
American Type Culture Collection, "ATCC CCL-86," organism: *Homo sapiens*; [online]; Manassas, VA [retrieved on Feb. 5, 2019] from the Internet. Retrieved from the Internet: https://www.google.com/search?client=firefox-b-1-d&q=ATCC+CCL-86. pgs.
American Type Culture Collection, "ATTC No. CCL-213," organism: *Homo sapiens*; [online]; Manassas, VA [retrieved on Feb. 5, 2019] from the Internet. Retrieved from the Internet: https://www.atcc.org/products/all/CCL-213.aspx; 3 pgs.
American Type Culture Collection, "ATTC No. CRL-1420," organism: *Homo sapiens*; [online]; Manassas, VA [retrieved on Feb. 5, 2019] from the Internet. Retrieved from the Internet: https://www.atcc.org/products/all/CRL-1420.aspx; 3 pgs.
American Type Culture Collection, "ATTC No. HTB-38," organism: *Homo sapiens*; [online]; Manassas, VA [retrieved on Feb. 5, 2019] from the Internet. Retrieved from the Internet: https://www.atcc.org/products/all/HTB-38.aspx; 3 pgs.
American Type Culture Collection, "ATTC No. CRL-1435," organism: *Homo sapiens*; [online]; Manassas, VA [retrieved on Feb. 5, 2019] from the Internet. Retrieved from the Internet: https://www.atcc.org/products/all/CRL-1435.aspx#documentation; 3 pgs.
American Type Culture Collection, "ATTC No. CCL-240," organism: *Homo sapiens*; [online]; Manassas, VA [retrieved on Feb. 5, 2019] from the Internet. Retrieved from the Internet: https://www.atcc.org/products/all/CCL-240.aspx#documentation; 3 pgs.
Bachanova, "Phase I Study of a Bispecific Ligand-Directed Toxin Targeting CD22 and CD19 (DT2219) for Refractory B-cell Malignancies" 2015 *Clin Cancer Res.*, 21:1267-1272.
Barker, "Sequence Analysis Primer" Review, Jan. 1993 *Biophys J.*, 64:292.
Berman, "The Protein Data Bank" 2000, *Nucleic Acids Res.*, 28:235-242.
Brons, "Hierarchic T-cell help to non-linked B-cell epitopes" Nov. 1996 *Scandinavian journal of immunology*, 44:478-84.
Collier, "Diphtheria toxin: mode of action and structure" 1975 *Bacteriological reviews*, 39:54-85.

(Continued)

*Primary Examiner* — Sarvamangala Devi
(74) *Attorney, Agent, or Firm* — Mueting Raasch Group

(57) ABSTRACT

This disclosure provides a bispecific ligand directed toxin (BLT) that includes a diphtheria toxin (DT) molecule that has been mutated to create a DT molecule that induces less of an immune response than native diphtheria toxin. The deimmunized DT molecule is fused with targeting ligands to create a fusion protein that can selectively deliver the deimmunized DT to target cells to kill the target cells.

22 Claims, 15 Drawing Sheets
Specification includes a Sequence Listing.

(56) References Cited

OTHER PUBLICATIONS

DSMZ German Collection of Microorganisms and Cell Cultures (Accession No. ACC 483). Retrieved from the Internet: https://www.dsmz.de/catalogues/details/culture/ACC-483.html; Feb. 5, 2019. 2 pgs.
Eisenberg, "The helical hydrophobic moment: a measure of the amphiphilicity of a helix" Oct. 1982 *Nature*, 299:371-4.
Fogh, "One hundred and twenty-seven cultured human tumor cell lines producing tumors in nude mice" 1977 *Journal of the National Cancer Institute*, 59:221-6.
Frankel, "DAB389IL2 (ONTAK) fusion protein therapy of chronic lymphocytic leukaemia" 2003 *Expert opinion on biological therapy*, 3:179-86.
Frankel, "Anti-CD3 recombinant diphtheria immunotoxin therapy of cutaneous T cell lymphoma" 2009 *Current drug targets*, 10:104-9.
Gallagher, "Characterization of the continuous, differentiating myeloid cell line (HL-60) from a patient with acute promyelocytic leukemia" 1979 *Blood*, 54:713-733.
Hayes, "Isolation of malignant B cells from patients with chronic lymphocytic leukemia (CLL) for analysis of cell proliferation: validation of a simplified method suitable for multi-center clinical studies" 2010 *Leuk Res.*, 34:809-815.
He, "Effects of mutation at the D-JH junction on affinity, specificity, and idiotypy of anti-progesterone antibody DB3" Sep. 2006 *Protein science: a publication of the Protein Society*, 15:2141-8.
Hopp, "Prediction of protein antigenic determinants from amino acid sequences" Jun. 1981 *Proceedings of the National Academy of Sciences of the United States of America*, 78:3824-8.
Jain, "Delivery of novel therapeutic agents in tumors: physiological barriers and strategies" 1989 *J Natl. Cancer Inst.*, 81:570-57.
Jameson, "The antigenic index: a novel algorithm for predicting antigenic determinants" 1988 *Computer applications in the biosciences: CABIOS*, 4:181-6.
Jemmerson, "Multiple overlapping epitopes in the three antigenic regions of horse cytochrome c1" Jan. 1987 *J Immunol.*, 138:213-9.
Kaighn, "Establishment and characterization of a human prostatic carcinoma cell line (PC-3)" 1979 *Investigative urology*, 17:16-23.
Klein, "Surface IgM-kappa specificity on a Burkitt lymphoma cell in vivo and in derived culture lines" Jul. 1968 *Cancer research*, 28:1300-10.
Kreitman, "Immunotoxins in the treatment of hematologic malignancies" Jan. 2006 *Current drug targets*, 7:1301-11.
Lambotte, "Primary structure of diphtheria toxin fragment B: structural similarities with lipid-binding domains" Dec. 1980 *The Journal of cell biology*, 87:837-40.
Lin, "Expression cloning of human EGF receptor complementary DNA: gene amplification and three related messenger RNA products in A431 cells" 1984 *Science*, 224:843-8.
Morikawa, "Two E-rosette-forming lymphoid cell lines" Feb. 1978 *Int J Cancer* 21(2): 166-170.
Newman, "Patterns of antibody specificity during the BALB/c immune response to hen eggwhite lysozyme" Nov. 1992 *J Immunol.*, 149:3260-72.
Oh, "A Deimmunized Bispecific Ligand-Directed Toxin That Shows an Impressive Anti-Pancreatic Cancer Effect in a Systemic Nude Mouse Orthotopic Model" 2012 *Pancreas*, 41(5):789-96.
Oh, "Intracranial elimination of human glioblastoma brain tumors in nude rats using the bispecific ligand-directed toxin, DTEGF13 and convection enhanced delivery" Dec. 2009 *J Neurooncol.*, 95(3):331-342.
Oh, "A novel reduced immunogenicity bispecific targeted toxin simultaneously recognizing human epidermal growth factor and interleukin-4 receptors in a mouse model of metastatic breast carcinoma" 2009 *Clinical cancer research: an official journal of the American Association for Cancer Research*, 15:6137-47.
Onda, "Characterization of the B cell epitopes associated with a truncated form of Pseudomonas exotoxin (PE38) used to make immunotoxins for the treatment of cancer patients" 2006 *J Immunol.*, 177:8822-34.
Onda, "Recombinant immunotoxin against B-cell malignancies with no immunogenicity in mice by removal of B-cell epitopes" Apr. 2011 *Proc Natl Acad Sci USA*, 108(14):5742-7.
Pastan, "Recombinant toxins as novel therapeutic agents" 1992 *Annual review of biochemistry*, 61:331-54.
Pulvertaft, "Cytology of Burkitt's Tumour (African Lymphoma)" 1964 *Lancet*, 1:238-240.
Rosenberg, "Intersite helper function of T cells specific for a protein epitope that is not recognized by antibodies" 1997 *Immunological investigations*, 26:473-89.
Schmohl, "Heterodimeric bispecific single chain variable fragments (scFv) killer engagers (BiKEs) enhance NK-cell activity against CD 133+ colorectal cancer cells" 2015 *Targeted Oncology*, 11(3):353-361.
Schmohl, "Mutagenic Deimmunization of Diphtheria Toxin for Use in Biologic Drug Development" Oct. 2015 *Toxins (Basel)*:7(10): 4067-4082.
Schmohl, "Enhanced ADCC and NK Cell Activation of an Anticarcinoma Bispecific Antibody by Genetic Insertion of a Modified IL-15 Cross-linker" 2016 *Mol Ther.*, 24(7): 1312-1322.
Stish, "A bispecific recombinant cytotoxin (DTEGF13) targeting human interleukin-13 and epidermal growth factor receptors in a mouse xenograft model of prostate cancer" Nov. 2007 *Clinical cancer research: an official journal of the American Association for Cancer Research*, 13:6486-93.
Stish, "Design and modification of EGF4KDEL 7Mut, a novel bispecific ligand-directed toxin, with decreased immunogenicity and potent anti-mesothelioma activity" Oct. 2009 *British journal of cancer*, 101:1114-23.
Stish, "Anti-glioblastoma effect of a recombinant bispecific cytotoxin cotargeting human IL-13 and EGF receptors in a mouse xenograft model" Dec. 2008 *Journal of neuro-oncology*, 87:51-61.
Tamilvanan, "Clinical concerns of immunogenicity produced at cellular levels by biopharmaceuticals following their parenteral administration into human body" Aug. 2010 *Journal of drug targeting*, 18:489-98.
Tsai, "A novel bispecific ligand-directed toxin designed to simultaneously target EGFR on human glioblastoma cells and uPAR on tumor neovasculature" Jun. 2011 *Journal of neuro-oncology*, 103:255-66.
Tsuneoka, "Evidence for involvement of furin in cleavage and activation of diphtheria toxin" Dec. 1993 *The Journal of biological chemistry*, 268:26461-5.
Vallera, "Genetic alteration of a bispecific ligand-directed toxin targeting human CD19 and CD22 receptors resulting in improved efficacy against systemic B cell malignancy" 2009 *Leukemia research*, 33:1233-42.
Vallera, "Bioengineering a unique deimmunized bispecific targeted toxin that simultaneously recognizes human CD22 and CD19 receptors in a mouse model of B-cell metastases" 2010 *Molecular cancer therapeutics*, 9:1872-83.
Vallera, "Genetically designing a more potent antipancreatic cancer agent by simultaneously co-targeting human IL13 and EGF receptors in a mouse xenograft model" May 2008 *Gut*, 57:634-41.
Vallera, "Molecular modification of a recombinant, bivalent antihuman CD3 immunotoxin (Bic3) results in reduced in vivo toxicity in mice" 2005 *Leukemia research*, 29:331-41.
Yunis, "Human pancreatic carcinoma (MIA PaCa-2) in continuous culture: sensitivity to asparaginase" 1977 *International journal of cancer Journal international du cancer*, 19:128-35.
Zurawski, "Interleukin 13, an interleukin 4-like cytokine that acts on monocytes and B cells, but not on T cells" 1994 *Immunology today*, 15:19-26.

\* cited by examiner

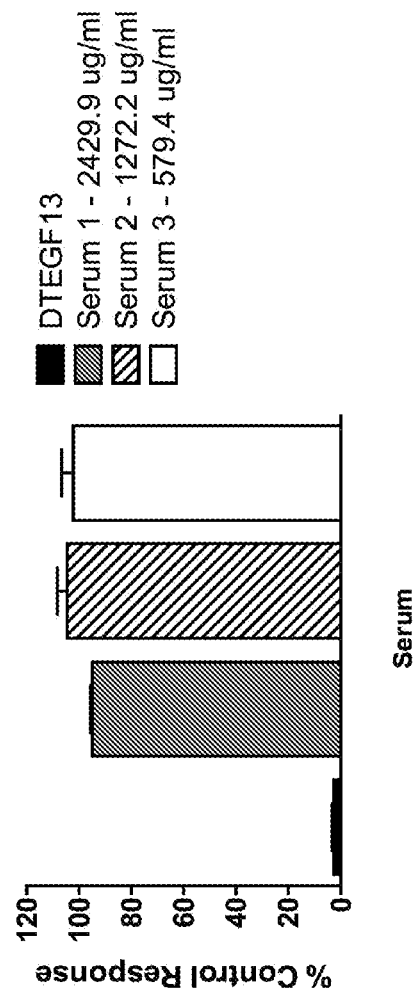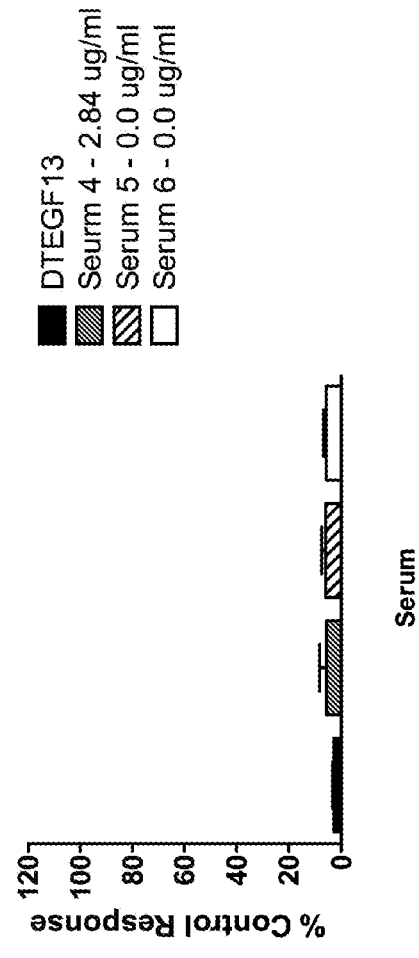
Fig. 6

Fig. 9

Alignment of Sequence_1: [dDt] with Sequence_2: [Sequence 2 from US8252897B2 amino acid.xpti]

similarity = 380/386 (98.45 %)

```
Seq_1     1  -GADDVVDSSKSFVMENFSSYHGTKPGYVDSIQKGIQKPKSGTQGNYDDDWKGFYSTDNK   59
             |||||||||||||||||||||||||||||||||||||||||||||||||||||||||||
Seq_2     1  MGADDVVDSSKSFVMENPSSYHGTKPGYVDSIQKGIQKPKSGTQGNYDDDWKGFYSTDNK   60

Seq_1    60  YDAAGYSVDNENPLSGKAGGVYKVTYPGLTMVLALKVDNAETIKKELGLSLTEPLMEQVG   119
             |||||||||||||||||||||||||||||||||||||||||||||||||||||||||||
Seq_2    61  YDAAGYSVDNENPLSGKAGGVYKVTYPGLTKVLALKVDNAETIKKELGLSLTEPLMEQVG   120

Seq_1   120  TEEFT▢RFGDGASRVVLSLPFAEGSSVEYINWWEQAKALSVELEINFETRGK▢QDAMY   179
             ||||| |||||||||||||||||||||||||||||||||||||||||||||| |||||
Seq_2   121  TEEFT▢RFGDGASRVVLSLPFAEGSSVEYINWWEQAKALSVELEINFETRGK▢QDAMY   180

Seq_1   180  BYMSQ▢CAGNRVRRSVGSSLSCTNLDWDVIRDKTKIKIESLKEHGP▢KNKMSESPNKTVS   239
             ||||| |||||||||||||||||||||||||||||||||||||||  |||||||||||
Seq_2   181  BYMQ ▢CAGNRVRRSVGSSLSCTNLDWDVIRDKTKIKIESLKEHGPL▢KNKMSESPNKTVS   240

Seq_1   240  BEKAI▢LBEEFHQTALEHPELSBLKTVTGTNPVFAGANYAAWAVNVAQVIDS▢TADNLEK   299
             ||||| ||||||||||||||||||||||||||||||||||||||||||||| |||||▢
Seq_2   241  BEKAI▢LBEEFHQTALEHPELSBLKTVTGTNPVFAGANYAAWAVNVAQVIDS▢TADNLEX   300

Seq_1   300  TPAALSILPGIGSVMGIADGAVHHNTEEIVAQSTALSSLMVAQAIPLVGELVDIGPAAYN   359
             |||||||||||||||||||||||||||||||||||||||||||||||||||||||||||
Seq_2   301  TPAALSILPGIGSVMGIADGAVHHNTEEIVAQSTALSSLMVAQAIPLVGELVDIGPAAYN   360

Seq_1   360  FVESIINLFQVVHNSYNRPAYSPGHG▢OPF   389
             ||||||||||||||||||||||||||
Seq_2   361  FVESIINLFQVVHNSYNRPAYSPGHK▢--   387
```

▢ =dDt mutation sites

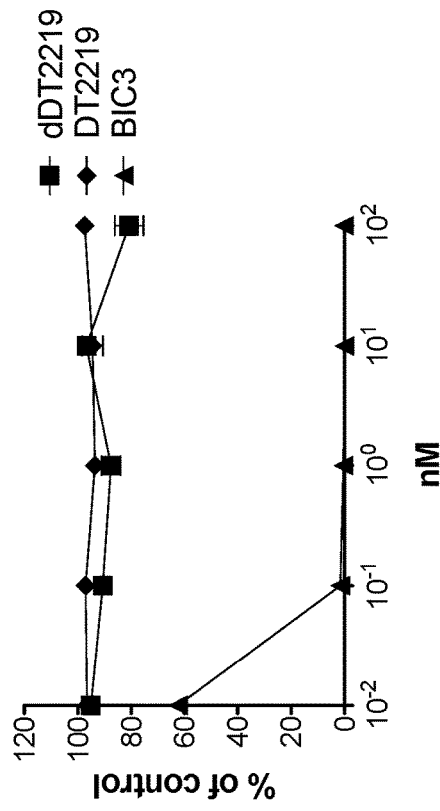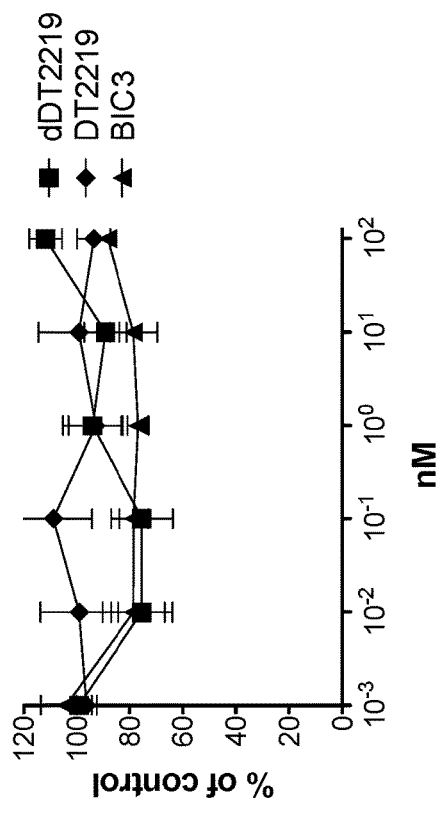
Fig. 12

Fig. 14
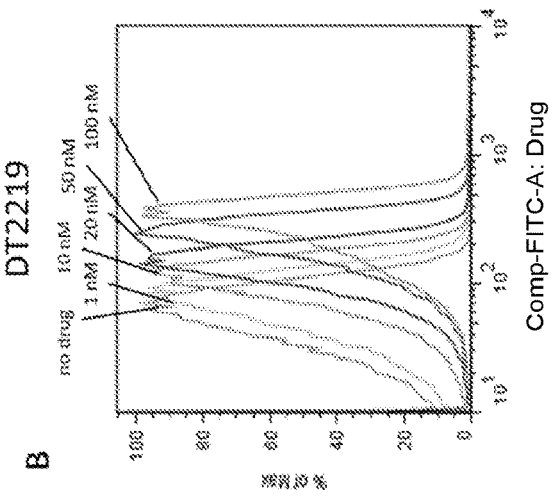
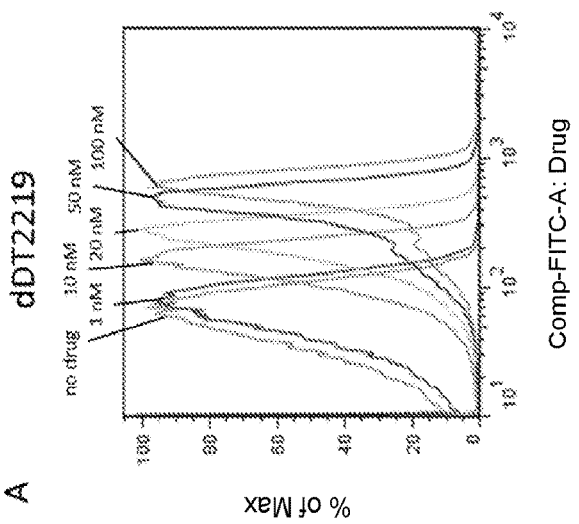
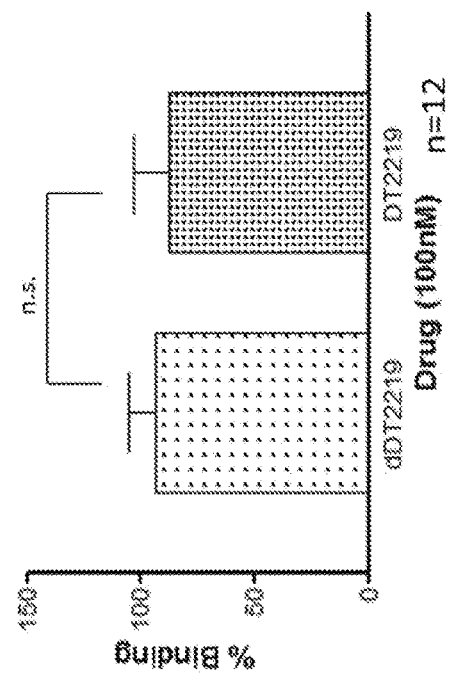
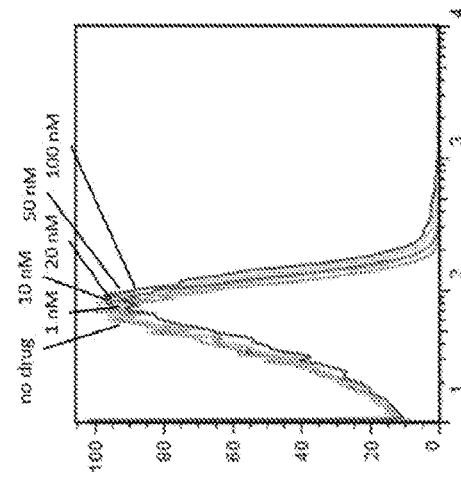

DEIMMUNIZED THERAPEUTIC COMPOSITIONS AND METHODS

CROSS-REFERENCE TO RELATED APPLICATION

This application is the § 371 U.S. National Stage of International Application No. PCT/US2016/054823, filed Sep. 30, 2016, which claims priority to U.S. Provisional Application No. 62/236,568, filed Oct. 2, 2015, each of which is incorporated by reference herein by reference in its entirety.

GOVERNMENT FUNDING

This invention was made with government support under CA036725 awarded by National Institutes of Health. The government has certain rights in the invention.

SEQUENCE LISTING

This application contains a Sequence Listing electronically submitted via EFS-Web to the United States Patent and Trademark Office as an ASCII text file entitled "2016-09-30-SequenceListing_ST25.txt" having a size of 58 kilobytes and created on Sep. 30, 2016. The information contained in the Sequence Listing is incorporated by reference herein.

SUMMARY

This disclosure describes, in one aspect, an engineered polypeptide that includes a diphtheria toxin (DT) domain and a targeting domain. The DT domain includes the DT catalytic site and at least one amino acid substitution that decreases induction of anti-toxin antibodies compared to wild-type diphtheria toxin. The targeting domain includes a targeting moiety that selectively binds to a target.

In some embodiments, the targeting domain selectively binds to a component of a tumor cell. In some embodiments, the polypeptide can include two or more targeting domains and/or two or more targeting moieties In some embodiments, the DT domain includes at least three amino acid substitutions compared to the amino acid sequence of DT390.

In another aspect, this disclosure describes a method of killing a cell. Generally, the method includes contacting the cell to be killed with any embodiment of the polypeptide summarized above under conditions that allow the cell to internalize the polypeptide; and allowing the polypeptide to kill the cell. In various embodiments, the cell may be in vitro or in vivo.

In another aspect, this discloser describes a method of treating a subject having a tumor. Generally, the method includes administering to the subject any embodiment of the polypeptide summarized above in which the polypeptide includes a targeting domain selectively binds to a target present on cells of the tumor.

In another aspect, this discloser describes a method of deimmunizing a diphtheria toxin polypeptide. Generally, the method includes identifying hydrophilic amino acid residues positioned at the surface of the native diphtheria toxin polypeptide, constructing a modified diphtheria toxin polypeptide comprising a substitution of one of the identified hydrophilic amino acid residues, screening the modified diphtheria toxin polypeptide for biological function of the native diphtheria toxin polypeptide, and screening the modified diphtheria toxin polypeptide for induction of antibodies.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIGS. 6A and 6B. Neutralizing antibodies. Serum was collected from mice immunized with multiple injections of (A) parental DTEGF13 or (B) dDTEGF13 on day 56. Serum from individual mice was incubated with cells treated with a known inhibitory concentration of DTEGF13 in order to test for neutralization. Proliferation assays were performed by measuring tritiated thymidine uptake after 72 hours. The serum concentration of IgG anti-toxin that was measured for each serum on day 56 is shown. There is a correlation between serum levels and the presence of neutralizing antibody.

FIG. 9. Exemplary deimmunized DT amino acid sequence (Sequence_1; SEQ ID NO:1) compared to non-deimmunized DT amino acid sequence (Sequence_2; SEQ ID NO:2). Boxes show exemplary sites of amino acid substitutions.

FIG. 10. Construction and purification of dDT2219. (A) The dDT2219 coding region has an NcoI restriction site, the first 390 amino acids of the deimmunized DT molecule (dDT390), spliced to an anti-CD22 scFv, spliced to an anti-CD19 scFv, and to the XhoI restriction site. (B) shows the absorbance trace for dDT2219. The arrow marks the product of interest. (C) Size comparison was performed via SDS-PAGE gel and COOMASSIE blue staining. dDT2219, DT2219, molecular weight standard [MW standards], an anti-CD19 scFv spliced to an anti-CD22 scFv devoid of DT [2219] and diphtheria toxin alone [DT] were compared in size. dDT2219 is 97.5 kD in size. (D) Purity was over 90% after size exclusion column purification (product is marked between C3 and C6 fraction).

FIG. 11. Activity and kinetics of dDT2219. The kinetics and activity of (A) dDT2219, (B) DT2219 and (C) BIC 3 (a monospecific anti-CD3 scFv conjugated with DT) was evaluated using Daudi cells. Comparison was performed after an incubation time of 12 hours, 24 hours, or 36 hours in an increasing concentration of the drugs as labeled. Whereas a slightly enhanced activity in higher concentrations (1 nM, 10 nM, 100 nM) of DT2219 compared to dDT2219 was observed, no effect was seen with the negative control BIC3 (Daudi cells express CD19 and CD22 but not CD3). In (D) a direct comparison was performed with a different Burkitt Lymphoma cell line (Raji cells). Whereas for dDT2219 and DT2219 efficacy was documented, no effect was seen for BIC3 (Raji cells express CD19 and CD22 but not CD3).

FIG. 12. Specificity of target cell elimination. In order to evaluate specificity of dDT2219, (DT2219 and BIC3 are controls), proliferation assays were performed. After exposure of the respective drugs to HPB-MLT cells (a T-cell leukemia cell line that expresses CD3), inhibition of proliferation was only seen for BIC3. (top panel) When HL-60 cells ($CD3^-$, $CD22^-$, $CD19^-$ acute promyeloid leukemia cell line) were exposed to the respective drugs, no inhibition of proliferation was detectable. (bottom panel)

FIG. 13. Evaluation of specific binding. Daudi cells were exposed to FITC-labeled dDT2219 (A) or DT2219 (B) in labeled concentrations. Fluorescence showed a binding of <85% for dDT2219-FITC and 75% for DT2219-FITC. Furthermore, Daudi cells were again exposed to increasing concentrations of dDT2219-FITC and DT2219-FITC with the identical unlabeled drugs in 100 nM, 200 nM, or 500 nM. Both FITC labeled drugs showed reduction in binding due to specific blocking of the unlabeled constructs.

FIG. 14. Binding in CLL. Patient-derived CLL samples were exposed to FITC-labeled dDT2219, DT2219 and an anti-EpCAM scFv (control). (A), (B) and (C) show results after exposure of increasing concentrations of the respective drugs as labeled. (D) Patient-derived CLL samples were exposed to FITC-labeled dDT2219 or DT2219. A direct comparison of the binding characteristics with 100 nM of the respective construct showed a statistically not different binding of 93±3.5% and 88±4.4% for the dDT2219 and the DT2219 group respectively (p=0.25), (n=12).

FIG. 15. Neutralizing antibodies. Fourteen BALB/c immune competent mice were divided into two groups with seven mice respectively. Both groups were intraperitoneally vaccinated with dDT2219 (experimental group) or DT2219 (control group) and bleed on days 21, 35, 49, 63, 77, 99, 160. Sera were evaluated by performing an ELISA detecting α-DT390 antibodies. (A) All evaluated days showed a significantly lower concentration of α-DT390 antibodies in the dDT2219 group. (B) To evaluate functionality of detected antibodies a neutralization assay was performed using Raji targets. The dDT2219 group showed a significantly lower amount of functional neutralizing antibodies. (C, D) In the group which was immunized with DT2219, six of seven mice (mouse 2 to 7) developed a high titer of functional neutralizing antibodies whereas two of seven mice (mouse 3 and 7) developed functional antibodies in the group treated with dDT2219.

DETAILED DESCRIPTION OF ILLUSTRATIVE EMBODIMENTS

This disclosure describes compounds, compositions, and methods that involve deimmunized targeted toxins. The use of biological drugs can be limited because they can be recognized as foreign by the human immune system. This can be particularly true of bacterial proteins such as, for example, diphtheria toxin (DT). Diphtheria toxin has promise as a targeted toxin, but even federal drug administration (FDA) approved DT-based drugs such as denileukin diftitox (ONTAK, Eisai Co., Ltd., Tokyo, Japan) can elicit anti-toxin responses after multiple treatments. Furthermore, those who receive diphtheria, tetanus, and pertussis (DPT) immunization at an early age have a greater likelihood of generating an anti-toxin response on multiple treatment with DT-based drugs. DT targeted toxins (TT) have nevertheless proven effective in eliciting anti-cancer responses in many different animal models and in patients. Thus, pursuit of a deimmunized form of the toxin has been considered a desirable, but unattainable goal.

Diphtheria toxin is a 535 amino acid protein (mw 58.3 kDa), having two functional domains. The C-terminal B domain binds most eukaryotic cells. The B domain may be removed to form DT390 and/or replaced with ligands to form a DT targeted toxin. The N-terminal A domain includes the catalytic region that ADP-ribosylates elongation factor 2 (EF-2).

DTEGF13 is a bispecific ligand directed toxin (BLT) that includes truncated DT (DT390) and two ligands. The ligands include IL-13 and epidermal growth factor (EGF). The ligands bind to unrelated receptors. EGF binds to epidermal growth factor receptor (EGFR), a transmembrane signaling protein from the erbB family. EGFR is overexpressed on a range of carcinomas including carcinomas of the prostate, pancreatic, breast, and/or lung. IL-13 is a pleiotropic lymphokine and its receptor is overexpressed on tumors, B cells, and monocytes. DTEGF13 binds to its target via the EGF and IL-13 ligands, and once internalized it is toxic to target cells. In vivo, DTEGF13 is effective locally and systemically against cancers including but not limited to prostate, glioblastoma, and pancreatic carcinomas in local and systemic xenograft models. Thus, DTEGF13 generates an anti-diphtheria toxin response when injected in vivo and provides a model for deimmunization.

Hydrophilic amino acids having surface positions, as derived from an x-ray crystallographic model, away from the NAD-ribosylating catalytic site were selected for point mutation to create a deimmunized DT molecule of the invention. The mutants were sequentially screened for those that underwent screening for minimal activity loss. Candidate mutants with at least seven mutations were tested for their ability to generate anti-toxin IgG antibody when given multiple injections in animal models. Despite multiple immunizations, the deimmunized DTEGF13 (dDTEFG13; SEQ ID NO:8) showed reduced anti-toxin induction when compared to the non-mutated parental form.

Figure 1:
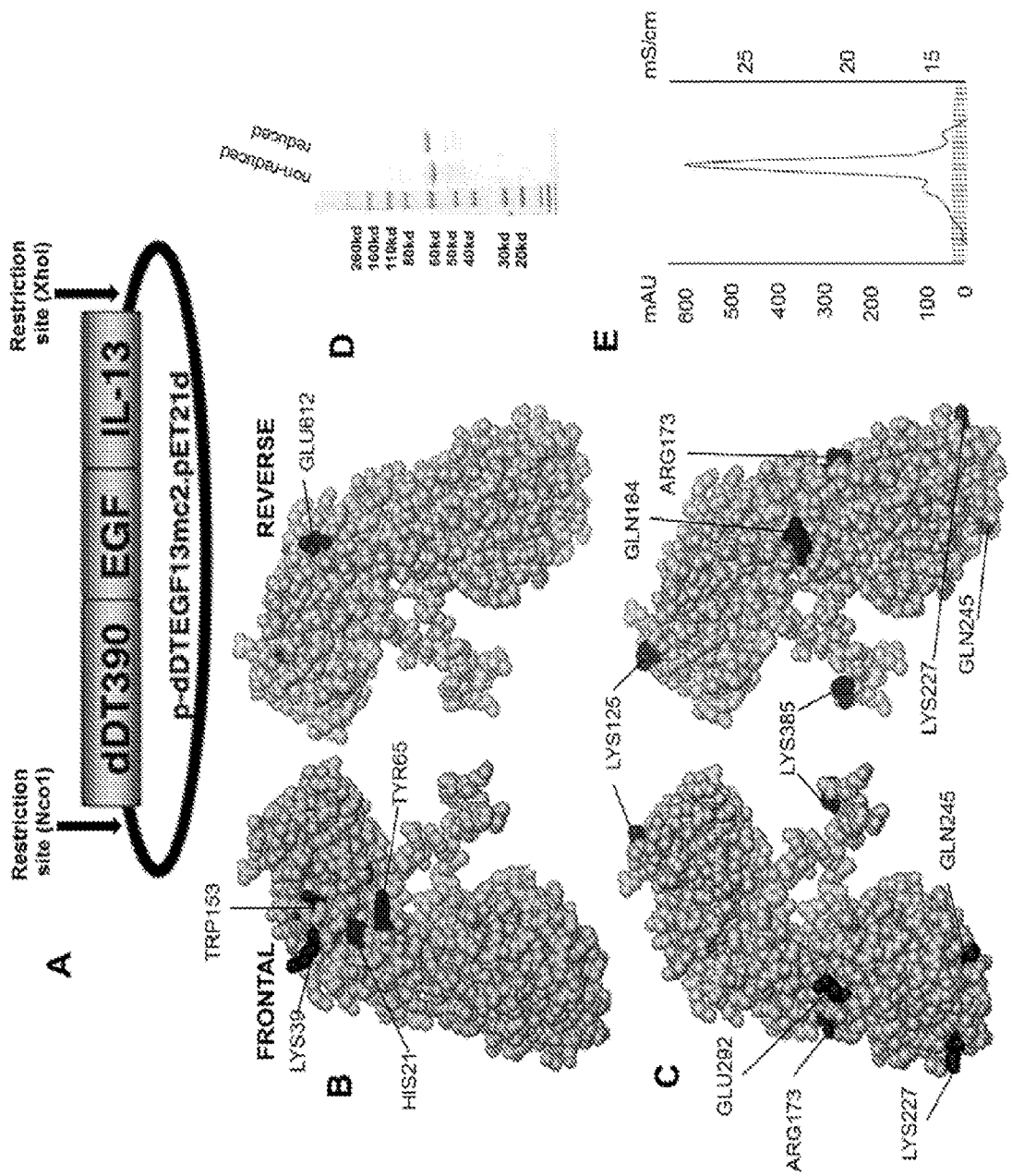
FIG. 1A to 1E. Construction of the plasmid containing the dDTEGF13 gene. (A) The pET expression vector containing the dDTEGF13 coding sequence (SEQ ID NO:13). The PyMol sphere graphic was generated by downloading the Protein Data Bank (RCSB PDB; Berman et al., 2000, *Nucleic Acids Res* 28:235-242) x-ray crystallographic structure of diphtheria toxin (DT; PBD ID: 1MDT) into the PyMOL 3D molecular modeling program (Schrödinger, LLC, New York, N.Y.). Shown is a frontal view of the protein and a 180° reverse view of the molecule. (B) Amino acids associated with ADP-ribosylation (catalytic site) are blackened. (C) The amino acids that were mutated for deimmunization are blackened. (D) SDS-PAGE gel analysis was performed to confirm the size and purity and stained with COOMASSIE blue. Lane 1—Molecular weight standards, Lane 2—dDTEGF13 non-reduced, Lane 3—dDTEGF13 reduced. The gel was stained using COOMASSIE blue. (E) An HPLC trace for the purified drug is also shown illustrating mostly a single peak obtained from a TSK3000 size exclusion column. Only the single peak was collected resulting in a >95% purity.

FIG. 1A shows the dDEGF13 plasmid construct and a PyMol spherical model of x-ray crystallographic structure in both front and reverse (180°) positions. Amino acids in the active site are shown in FIG. 1B. FIG. 1C shows the seven mutated amino acids for deimmunization, darkened so their surface position on the molecule can be easily visualized. SDS-PAGE gel analysis of dDTEGF13 with a purity of greater than 95% as determined by COOMASSIE blue staining is shown in FIG. 1D. Molecular weight size is estimated at 68.9 kDa from molecular weight standards.

Based on the molecular model derived from the x-ray crystallographic structure, twenty amino acid residues located in prominent surface positions were identified. A series of eight mutants were generated, each having three point mutations. Thus, the entire series probed 24 point mutations. Alanine and serine substitution were employed. The mutants were screened for activity loss using a standard, highly reproducible proliferation inhibition assay measuring thymidine uptake.

Figure 2:
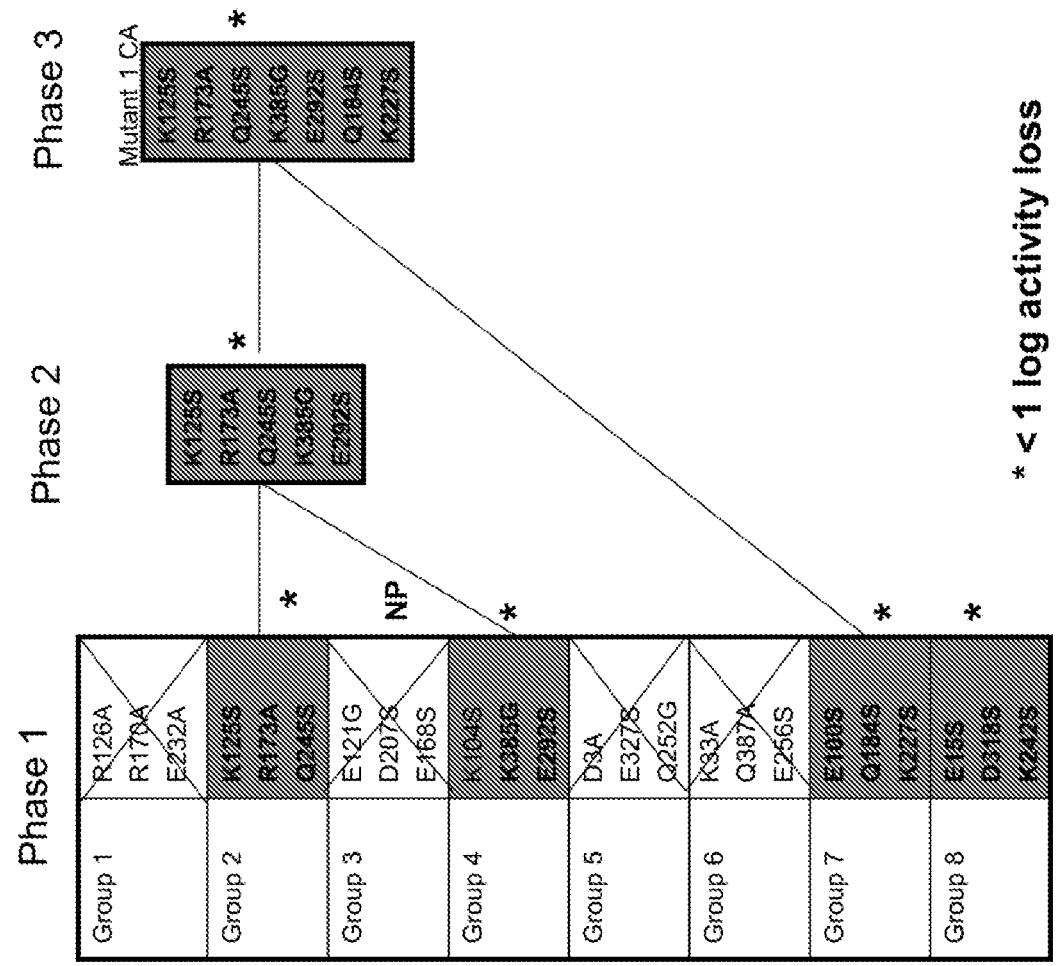
FIG. 2. Three-phase strategy for producing and screening various DTEGF13 mutants to achieve deimmunization. In Phase 1, eight triple mutants were synthesized and purified. Four of these showed less than a log of activity loss in an in vitro screening assay compared to the non-mutated parental control. In Phase 2, mutations were combined to generate a quintuple mutant that still had less than a log of activity loss compared to parental. In Phase 3, a septuple mutant still had less than a log of activity loss. Glycine, alanine, and serine substitution were employed.

FIG. 2 illustrates which of the mutants exhibited minimal activity losses and were subsequently combined with other mutants (Phase 1). Point mutations of mutants that exhibited less than a log loss were combined on the same molecule until DTEGF13, with seven mutations in separate areas of the molecule and less than a log of reduced activity in in vitro proliferation assays, was obtained (Phase 3). This mutant, shown in FIG. 1A, was subsequently tested for its ability to generate an anti-toxin response in immunocompetent mice.

Figure 3:
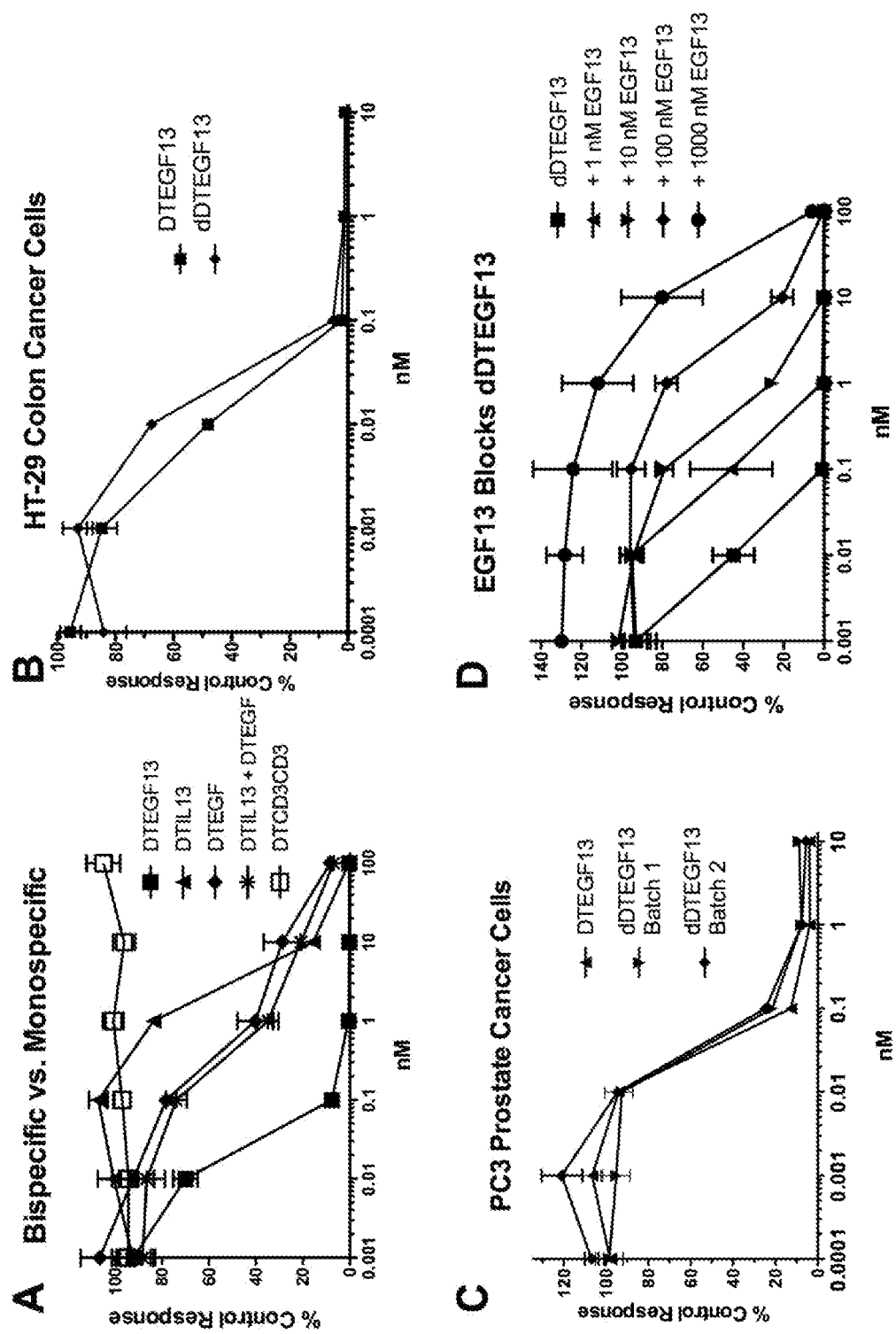
FIG. 3A to 3D. In vitro activity of dDTEGF13. (A) Bispecific DTEGF13 and its monospecific counterparts were tested and compared for their reactivity against MiaPaCa-2 cells. Proliferation assays were performed by analyzing $^3$H-thymidine uptake after a 72-hour incubation with targeted toxins. Data are reported as percent control response. Each data point represents an average of triplicate measures ±S.D. Deimmunized DTEGF13 and non-mutated parental DTEGF13 were tested and compared for activity against (B) HT-29 colon and (C) PC-3 prostate carcinoma cells in thymidine uptake assays. (D) A blocking assay was performed in which MiaPaca-2 pancreatic cancer cell lines were incubated with an inhibitory dose of DTEGF13 and then blocked with increasing concentration of EGF13 ligand devoid of toxin. Thymidine uptake was then measured.
Figure 4:
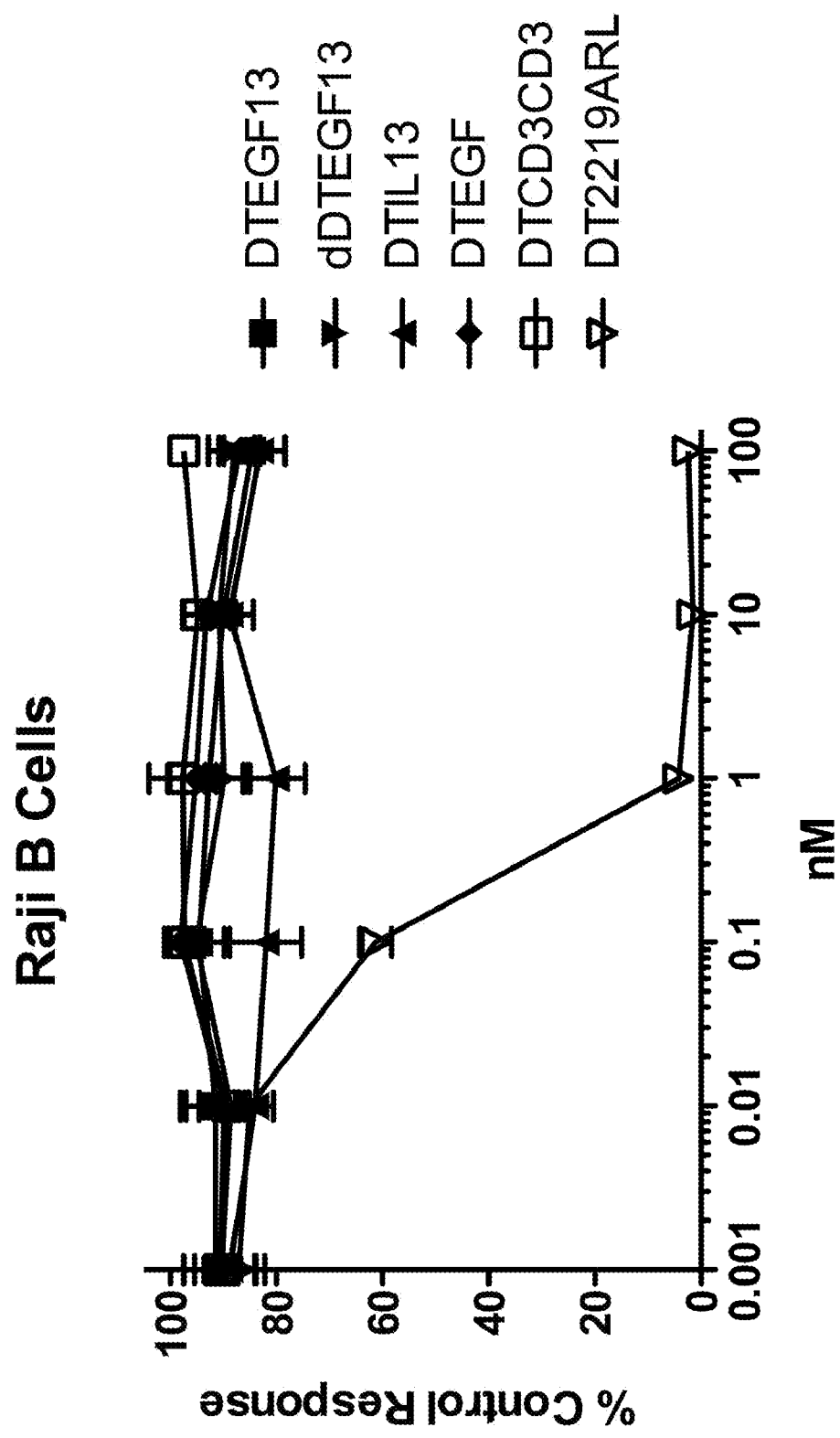
FIG. 4. In vitro activity of dDTEGF13 against Raji Cells. Bispecific dDTEGF13 and its monospecific counterparts were tested for their reactivity against Raji B cells. Proliferation assays were performed by analyzing $^3$H-thymidine uptake after a 72-hour incubation with targeted toxins. Data are reported as percent control response.

FIG. 3A shows that the bispecific ligand directed toxin DTEFG13 is very potent with and $IC_{50}$ of 0.019 nM on the $EGF^+IL13^+$ cell line MDA-MB-23 breast carcinoma cell line and has greater activity than its monospecific counterparts in the in vitro proliferation screening assay. In addition, FIG. 3B shows that dDTEGF13 has similar activity to the non-mutated parental control against the HT-29 human colon cancer carcinoma cell line. FIG. 3C shows that the same was true when dDTEGF13 and non-muted parental was tested against the PC-3 prostate carcinoma. FIG. 3D shows that the EGF13 ligand portion of dDTEGF13 molecule was mediated by its selective binding to target cells since DTEGF13 was blockable with EGF13 ligand devoid of toxin against MiaPaCA-2 cells. FIG. 4 shows that dDTEGF13 did not inhibit the EGFR-IL13R-control B cell line Daudi, but a positive control anti-B cell BLT called DT2219ARL (Vallera et al., 2009, *Leuk Res* 33:1233-1242) did inhibit. These data indicate activity is mediated through the selective binding of the ligands.

To determine whether DTEGF13 had been successfully deimmunized, groups of immunocompetent BALB/c mice ($H-2^d$) were immunized weekly with 0.25 µg of either mutated dDTEGF13, or non-mutated parental DTEGF13. Animals were immunized intraperitoneally over a period of 82 days. Serum samples were obtained weekly and analyzed using ELISA to detect anti-dDTEGF 13 IgG. The results of the immunization experiment are summarized in FIG. 5A, which shows statistical differences between the anti-toxin responses of the group of mice immunized with dDTEGF13 MC2 and the parental control. After 12 immunizations (day 82), the dDTEGF13 MC2 group showed minimal antibody response, while the parental group had an average anti-DT390 response of greater than 1,500 µg/ml. In order to determine whether anti-toxin serum levels could be reduced in a second strain of mice that presents antigens differently, the same experiment was repeated with C57BL/6 mice with a different H-2 haplotype ($H-2^b$). The results were nearly identical (FIG. 5B).

Figure 5:
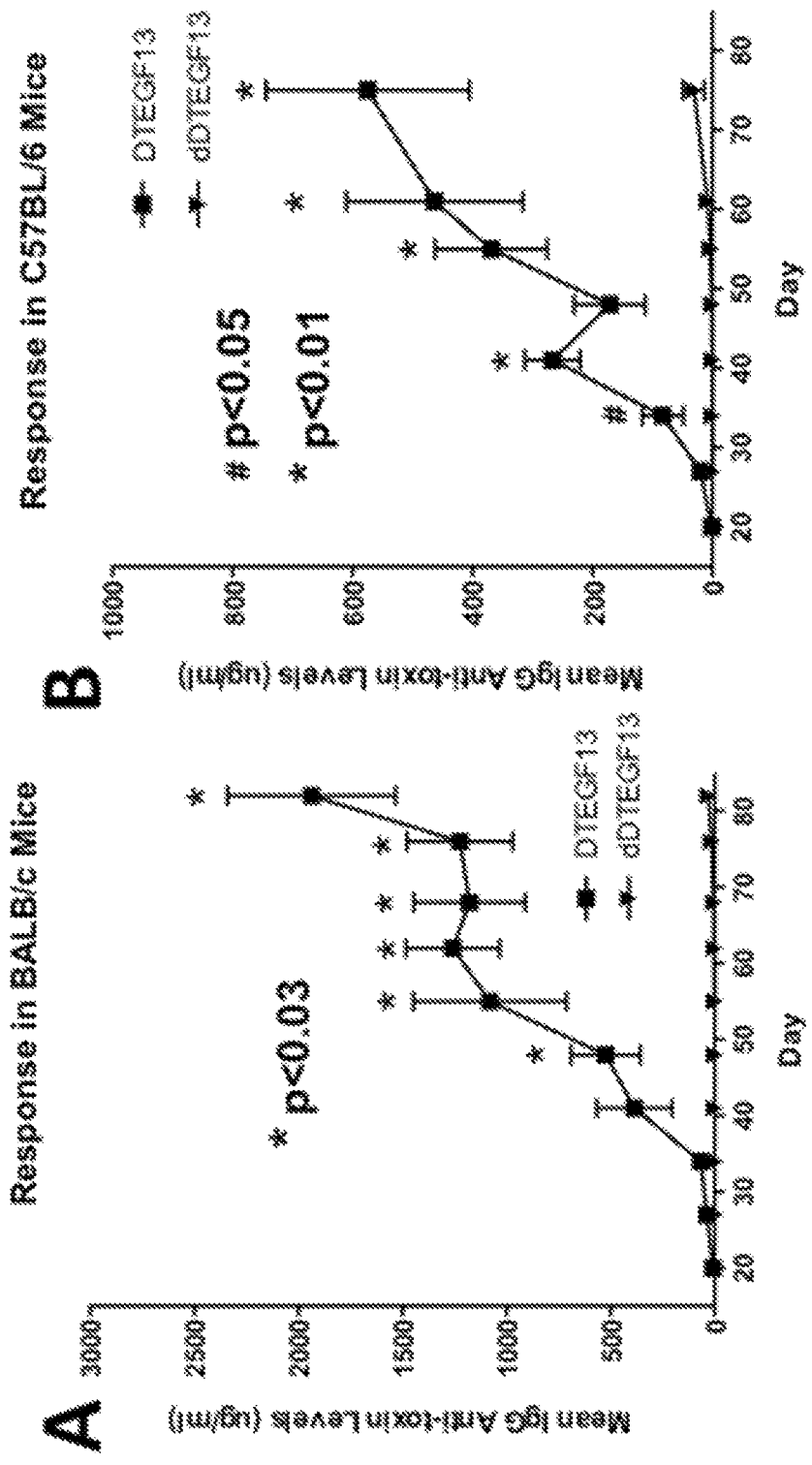
FIGS. 5A and 5B. The immunogenicity of dDTEGF13. The immune response to deimmunized dDTEGF13 and non-mutated parental drug was determined by measuring anti-DT390 serum IgG on weekly samples of mice immunized with 0.25 µg of DTEGF13 (n=5) or dDTEGF13 (n=5). Measurements were made using an indirect ELISA and quantification of antibodies was determined using a standard curve generated with highly purified, high titer anti-DT antibody. (A) Response in BALB/c mice; (B) Response in C57BL/6 mice.

To determine if neutralizing antibodies were present in the sera from immunized mice, sera from the mice in FIG. 5A were added to a known inhibitory concentration 1000 ng/ml of dDTEGF13. The treated cells were then tested for tritiated thymidine uptake in proliferation assays. FIG. 6A shows the percent control response of treated MiaPaCa-2 cells and then the response of cells treated with day 56 serum from three different mice immunized multiple times with parental DTEGF13. High IgG serum anti-toxin levels in these mice (2,429 µg/ml, 1,272 µg/ml, and 579 µg/ml) correlated with high neutralizing activity. In contrast, FIG. 6B shows the response of cells treated with day 56 serum from three different mice immunized multiple times with dDTEGF13. The low serum anti-toxin levels correlated with the lack of neutralizing activity. These data indicate that neutralizing antibodies were not present at day 56 in the serum of mice immunized with dDTEGF13.

Figure 7:
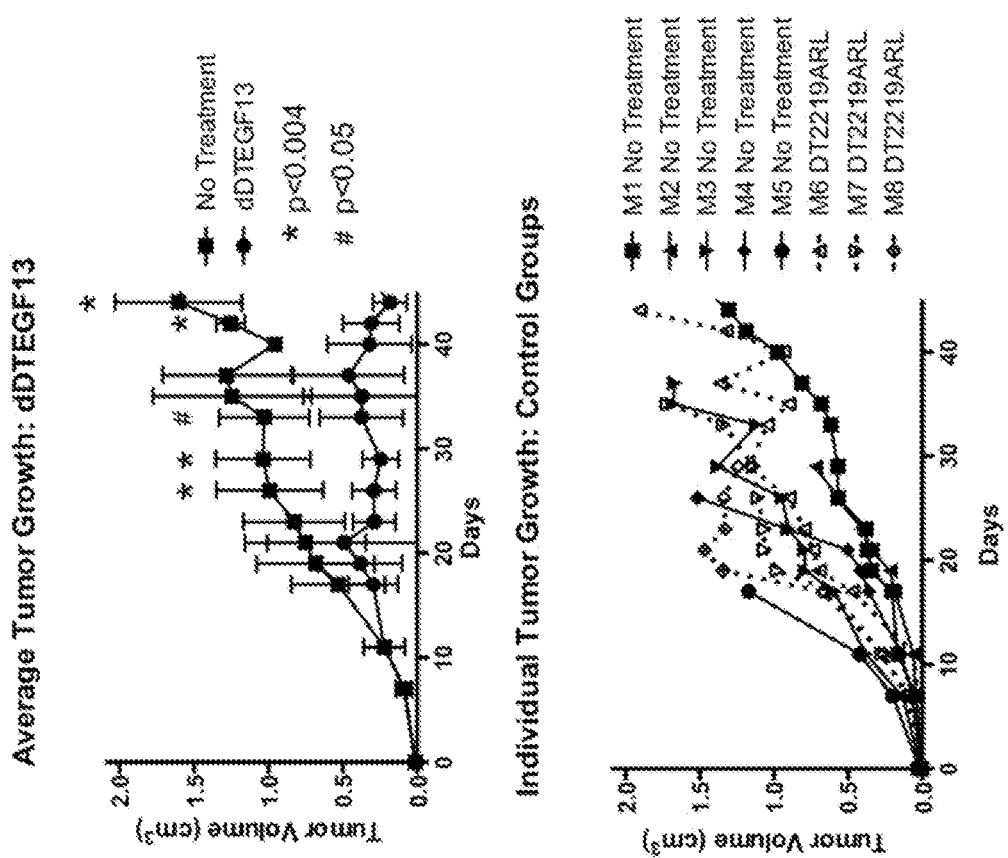
FIG. 7. The effect of treatment of established PC-3 flank tumors with dDTEGF13. Nude mice bearing PC-3 flank tumors were treated intratumorally with dDTEGF13, control DT2219ARL, or untreated. Tumors were treated with 12 injections of dDTEGF13. Average tumor volumes are shown for each treatment group (top panel). Individual tumor volumes are shown for both the irrelevant control BLT treated group (DT2219ARL) and the untreated mice. The growth of individual tumors is plotted over time (bottom panel).
Figure 8:
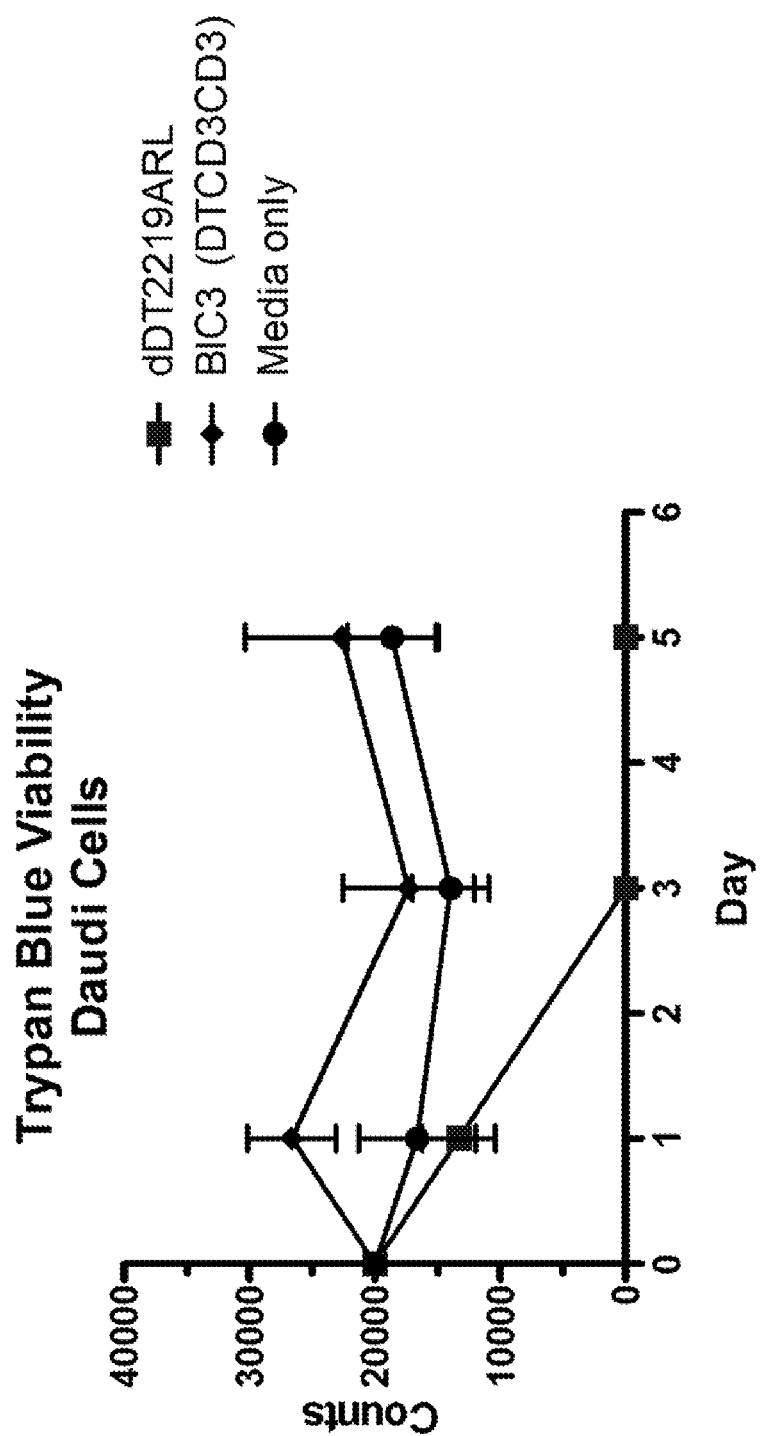
FIG. 8. In vitro activity of dDT2219 (SEQ ID NO:3). dDT2219 was tested in a TRYPAN blue viability assay in which a different cell line, CD22+CD19+ Daudi cells were plated and then 10 nM drug was added to the plate. Viability was determined daily. Dead cells take up TRYPAN blue dye, while live cells do not. Cells were visually counted using a hemocytometer. No cells survived dDT2219 treatment after three days. Cells treated with Bic3 were minimally affected.

To test the ability of dDTEGF13 to inhibit tumor growth in vivo, PC-3 cells were injected into the flank of nude mice. Once the tumors were established and palpable, mice were treated with multiple intratumoral injections. dDTEGF13 was studied in a mouse model because the human EGF and IL-13 (of DTEGF13) reacts with mouse EGFR and IL13R, respectively. The upper panel of FIG. 7 shows mean tumor volume data from the first experiment in which groups of mice were given injections (0.25 µg/injection) of either no treatment or treatment with dDTEGF13 on days 0, 1, 14, 21, 28, 35, 42, 49, 56, 63, 70, 77. The lower panel of FIG. 7 shows tumor growth of individual control mice. Control mice were either untreated or treated with an irrelevant immunotoxin control, DT2219ARL. The multiple injections of dDTEGF13 were effective at preventing tumor growth compared to the negative controls until the experiment was terminated on day 45.

This disclosure therefore describes, in one aspect, a deimmunized DT targeted toxin polypeptide that may be used in molecular drug development. Generally, the polypeptide includes a deimmunized diphtheria toxin domain that includes the DT catalytic site and at least one targeting domain selected to selectively bind to a target cell. In some cases, the targeting domain can include a domain that selectively binds to a tumor cell target. As used herein, the term "deimmunized" refers to a polypeptide that has been modified to reduce the extent to which the polypeptide induces an immune response in the subject to which it is administered as compared with a molecule that has not been deimmunized. In some cases, an antibody response to the DT targeted toxin molecule is measured. In one embodiment, antibody induction can be characterized in terms of antibody production induced in an immunocompetent mouse strain. Also, as used herein, the term "selectively" refers to having a differential affinity—e.g., greater than a general non-selective affinity—to any degree toward a particular desired target. An exemplary targeting domain can include a sufficient portion of a ligand or binding moiety, such as, for example, EGF, IL-13, anti-CD19, and/or anti-CD22, to selectively bind to its receptor that is expressed by a target cell. The resulting polypeptide exhibits measurable diphtheria toxin toxicity with reduced induction of anti-toxin antibodies in immunocompetent mice compared to wildtype diphtheria toxin. The polypeptide may be useful as a drug effective against, for example, neoplastic conditions such as pancreatic cancer, breast cancer, and glioma.

In some embodiments, a deimmunized DT molecule can include at least one amino acid substitution compared to DT390 (or full length DT). Thus, a dDT molecule can have at least one, at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, at least 21, at least 22, at least 23, at least or 24 mutations relative to DT390 or full length DT.

Thus, in some embodiments, the dDT molecule can include a substitution of at least three of amino acid residues 15, 100, 104, 125, 173, 185, 227, 242, 245, 292, 318, or 385. In one embodiment, the dDT molecule can include amino acid substitutions of K125, R173, and Q245. In another embodiment, the dDT molecule can include amino acid substitutions K125S, R173A, and Q245S. In another embodiment, the dDT molecule can include amino acid substitutions K104, K385, and E292. In another embodiment, the dDT molecule can include amino acid substitutions K104S, K385G, and E292S. In another embodiment, the dDT molecule can include amino acid substitutions E100, Q184, and K227. In another embodiment, the dDT molecule can include amino acid substitutions E100S, Q184S, and K227S. In another embodiment, the dDT molecule can include amino acid substitutions E15S, D318, and K242S.

In other embodiments, the dDT molecule can include at least five amino acids substitutions. Thus, in one embodiment, the dDT molecule can include amino acid substitutions K125, R173, Q245, K385, and E292. In another embodiment, the dDT molecule can include amino acid substitutions K125S, R173A, Q245S, K385G, and E292S.

In still other embodiments, the dDT molecule can include at least seven amino acid substitutions. Thus, in one embodiment, the dDT molecule can include amino acid substitutions K125, R173, Q245, K385G, E292, Q184, and K227. In another embodiment, the dDT molecule can include amino acid substitutions K125S, R173A, Q245S, K385G, E292S, Q184S, and K227S. In another embodiment, the dDT molecule can include amino acid substitutions K125S, R173A, Q245S, K385G, E292S, Q184S, and K227S.

While the dDT molecule is described using substitutions of serine, alanine, and/or glycine, these are exemplary molecules and one of skill in the art would be able to readily determine if other amino acids would provide a dDT molecule as described herein. For example, alanine, serine, and glycine may be used interchangeably to create dDT molecules that can be screened for activity and reduced immunogenicity, as described in the Examples herein.

While described above in the context of an exemplary embodiment in which the targeting domain can include a sufficient portion of EGF, IL-13, anti-CD19, and/or anti-CD22 to selectively bind to a desired target, the targeting domain can include any suitable targeting moiety. A "targeting moiety" refers to that portion of a compound (e.g., a ligand) that possesses target-selective affinity (e.g., toward a receptor for the ligand) that may be employed in a targeting domain. The targeting moiety may be, or be derived from, a ligand, an antibody, a cytokine, or an interleukin. In some cases, the targeting moiety may be, or be derived from, an agent that recognizes at least a portion of a tumor-specific marker such as, for example, a ligand that binds to a receptor that is, to some extent, specifically expressed by a target cell. In other cases, the targeting moiety may be an antibody or be derived from an antibody (e.g., at least enough of the immunospecific portion of an antibody—e.g., enough of a light chain—to provide some degree of immunospecificity).

In various embodiments, a targeting domain can include more than one targeting moiety. For example, an exemplary embodiment referred to herein as dDTEGF13 includes a first and second targeting moiety. The first targeting moiety includes a sufficient portion of EGF to selectively bind to EGFR, while the second targeting moiety includes a sufficient portion of IL-13 to selectively bind to IL-13 receptor. Likewise, an exemplary embodiment referred to herein as dDT2219 also includes a first and second targeting moiety. The first targeting moiety includes a sufficient portion of an anti-CD19 scFv to selectively bind to CD-19, while the second targeting moiety includes a sufficient portion of an anti-CD22 scFv to selectively bind to CD-22.

Thus, in various embodiments, the targeting domain can include a polypeptide that selectively binds to, for example, EGFR, HER2/neu, EpCAM, CD19, CD20, CD22, CD30, CD52, CD33, ROR-1, UPAR, VEGFR, CEA, UPA, LIV-1, SGN-CD70A, CD70, IL-3 alphA receptor, IL-4R, CD133, ROR1, mesothelin, TRAIL, CD38, CD45, CD74, or CD23.

The dDT2219 molecule is an engineered variant of DT2219 in which the diphtheria toxin domain of the molecule is replaced with a deimmunized DT domain. DT2219 is a recombinant fusion protein that contains the catalytic and translocation enhancing domain of diphtheria toxin (DT390) fused with bispecific single chain variable fragments (scFV) of antibodies targeting human CD19 and CD22 cell surface receptors. The protein is engineered so that the native binding region of DT is replaced by the more avidly bound scFV. After binding, CD19 and CD22 readily internalize to promote toxin entry into the cytosol, inhibition of protein synthesis, and/or subsequent apoptotic cell death.

CD19, a 95 kDa membrane glycoprotein, is ubiquitously present on the surface of all stages of B lymphocyte development and is also expressed on most B-cell mature lymphoma cells and leukemia cells. CD22 is 135-kDa glycoprotein expressed on B lineage lymphoid precursors, including precursor B acute lymphoblastic leukemia, and often is co-expressed with CD19 on mature B cell malignancies. DT mediates potent cell-cycle independent cell death and therefore can be particularly effective as an alternative therapy for chemotherapy refractory malignancies.

Figure 10:
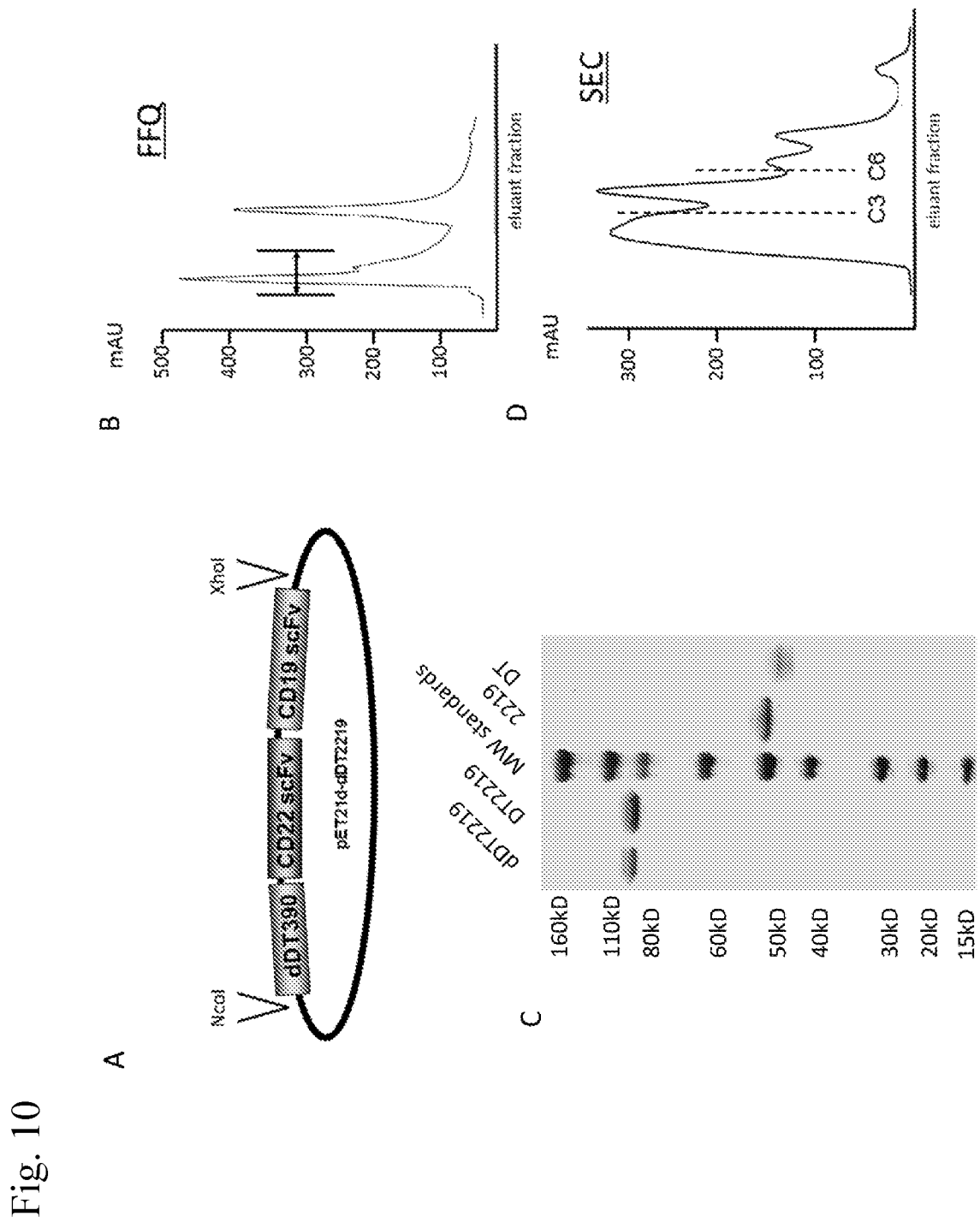

Construction of the dDT2219 molecule is shown in FIG. 10A. Polynucleotides encoding deimmunized DT (dDT390), the $V_H$ and VL regions of an anti-CD22, and the $V_H$ and VL regions of an anti-CD19 scFv were assembled as shown. The active fragments are connected via a EASGGPE (SEQ ID NO:4) and an ARL linker (SEQ ID NO:6), forming dDT2219. Absorbance tracing for dDT2219 eluted from an FFQ ion exchange column as the first phase in drug purification using a three-step elution protocol is displayed in FIG. 10B. The first peak eluted from the column represents the product of interest. SDS-PAGE gel (FIG. 10C) and COOMASSIE blue staining show purity after both ion exchange and size exclusion column purifications (FIG. 10D). The product is over 90% pure and with about 97.5 kD of size.

Figure 11:
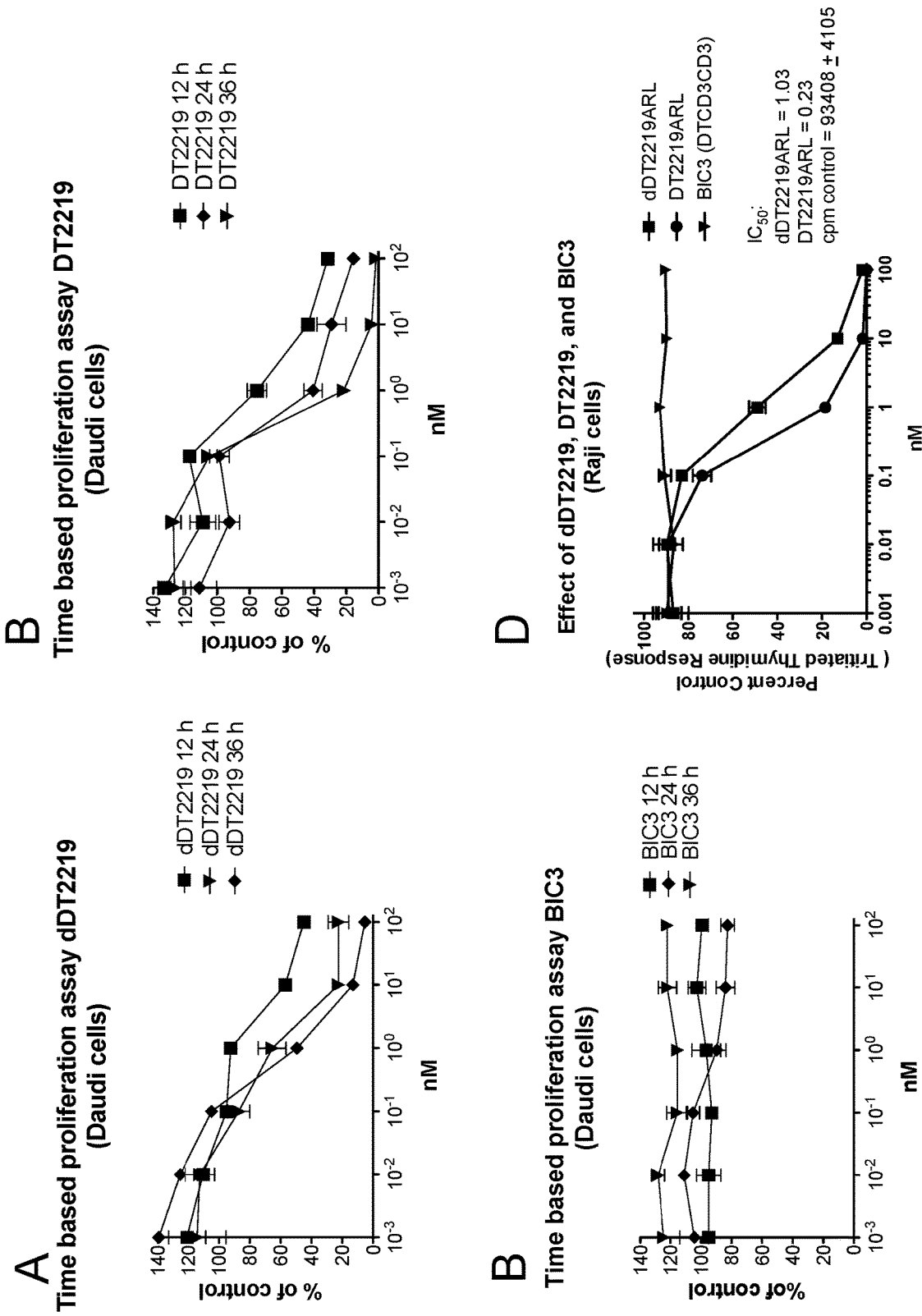

In order to show activity and kinetics of dDT2219 compared with the parental DT2219 form, proliferation assays we performed with the CD19$^+$/CD22$^+$ Burkitt lymphoma cell lines Daudi and Raji. Therefore, H$^3$-Thymidine uptake by Daudi cells was evaluated after exposure to the respective drug (FIG. 11A dDT2219, FIG. 11B DT2219) at 12 hours, 24 hours, and 36 hours and increasing concentrations (0.001 nM, 0.01 nM, 0.1 nM, 1 nM, 10 nM, and 100 nM). In higher concentrations (1-100 nM) after 24 and 36 hours, a slightly increased percentage of activity in the DT2219 group was visible, whereas in the control group with exposure to BIC3 no inhibition of proliferation at all time points was apparent (Daudi cells do not express CD3) (FIG. 11C). An additional Burkitt lymphoma cell line Raji was used to confirm reproducibility of the results. In a side by side proliferation assay using dDT2219, DT2219, and BIC3 for 72 hours of incubation, an IC$_{50}$ of 1.03 for dDT2219 and 0.23 for DT2219 was estimated. BIC3 again had no effect (FIG. 11D).

For verification of the specificity of dDT2219 (DT2219 and BIC were used as controls), a proliferation assay was performed with HPB-MLT cells (T-cell leukemia cell line that expresses CD3 but not CD19 or CD22) and dDT2219, DT2219, and BIC3 in labeled increasing concentrations. No effect after dDT2219 and DT2219 exposure was visible. Only BIC3 induced apoptosis (FIG. 12, upper panel). In the acute promyeloid leukemia cell line HL-60, which is negative for CD22, CD19 and CD3, no inhibition after treatment was seen (FIG. 12, lower panel).

Figure 13:
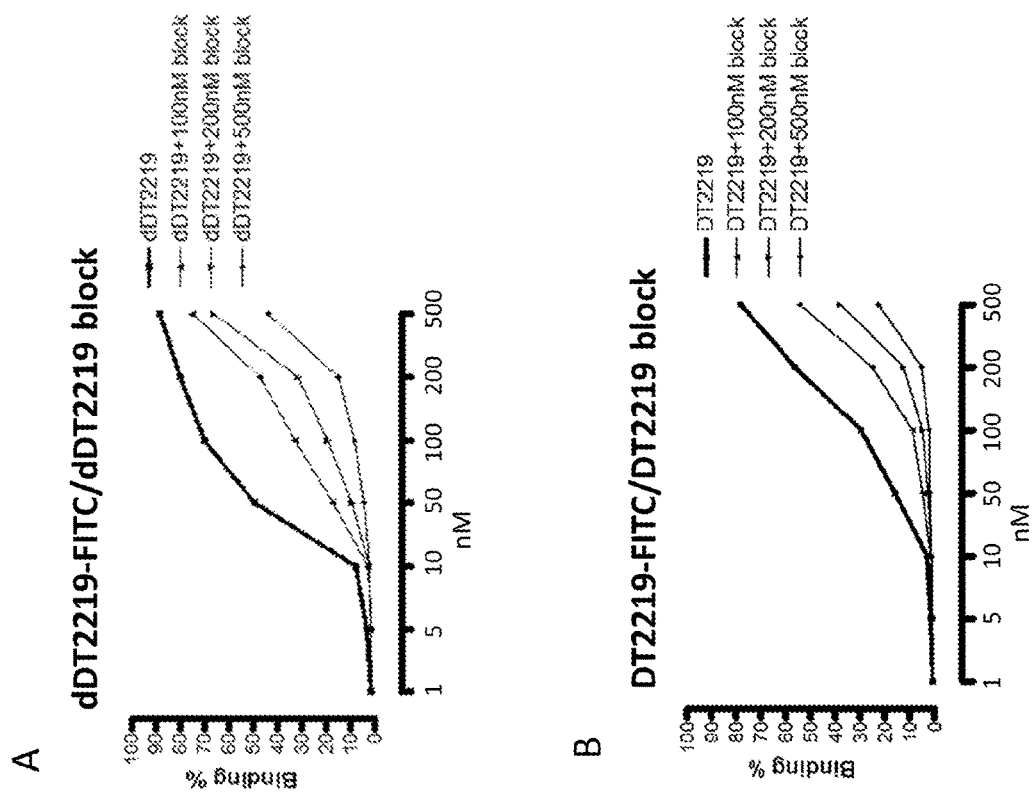

Binding and blocking characteristics were compared using flow cytometry. FITC-labeled dDT2219 (FIG. 13A) and DT2219 (FIG. 13B) were used in increasing concentrations (1 nM, 5 nM, 10 nM, 50 nM, 100 nM, 200 nM, or 500 nM) and incubated with Daudi cells. An increasing binding capability was seen up to over >85% for dDT2219 and >75% for DT2219. The same cells were treated with the same doses of dDT2219 or DT2219 and also exposed to 100 nM, 200 nM, or 500 nM of unlabeled dDT2219 or DT2219. The deimmunized as well as the parental unlabeled drug showed a sufficient binding and consecutive and dose dependent blocking of the FITC-labeled drugs, as seen in a reduction of fluorescence intensity.

In order to verify the binding capability in a clinical context, samples obtained from CLL patients were used to compare respective binding of dDT2219 and DT2219. Samples were exposed to increasing concentrations (no drug, 1 nM, 10 nM, 20 nM, 50 nM, or 100 nM) of FITC-labeled dDT2219 or DT2219. After gating on the CLL population, a dose-dependent increase in binding was seen for both constructs (FIGS. 14A and 14B). A FITC-labeled anti-EpCAM scFv was used as a negative control (FIG. 14C) and showed no binding. In a direct comparison between dDT2219 and DT2219, each patient sample was exposed to 100 nM of dDT2219 or DT2219. The mean fluorescence (representing binding) seen in all 12 CLL samples was 93% and 88% with no significant differences between the groups (p=0.25) (FIG. 14D), implying identical binding characteristics.

Figure 15:
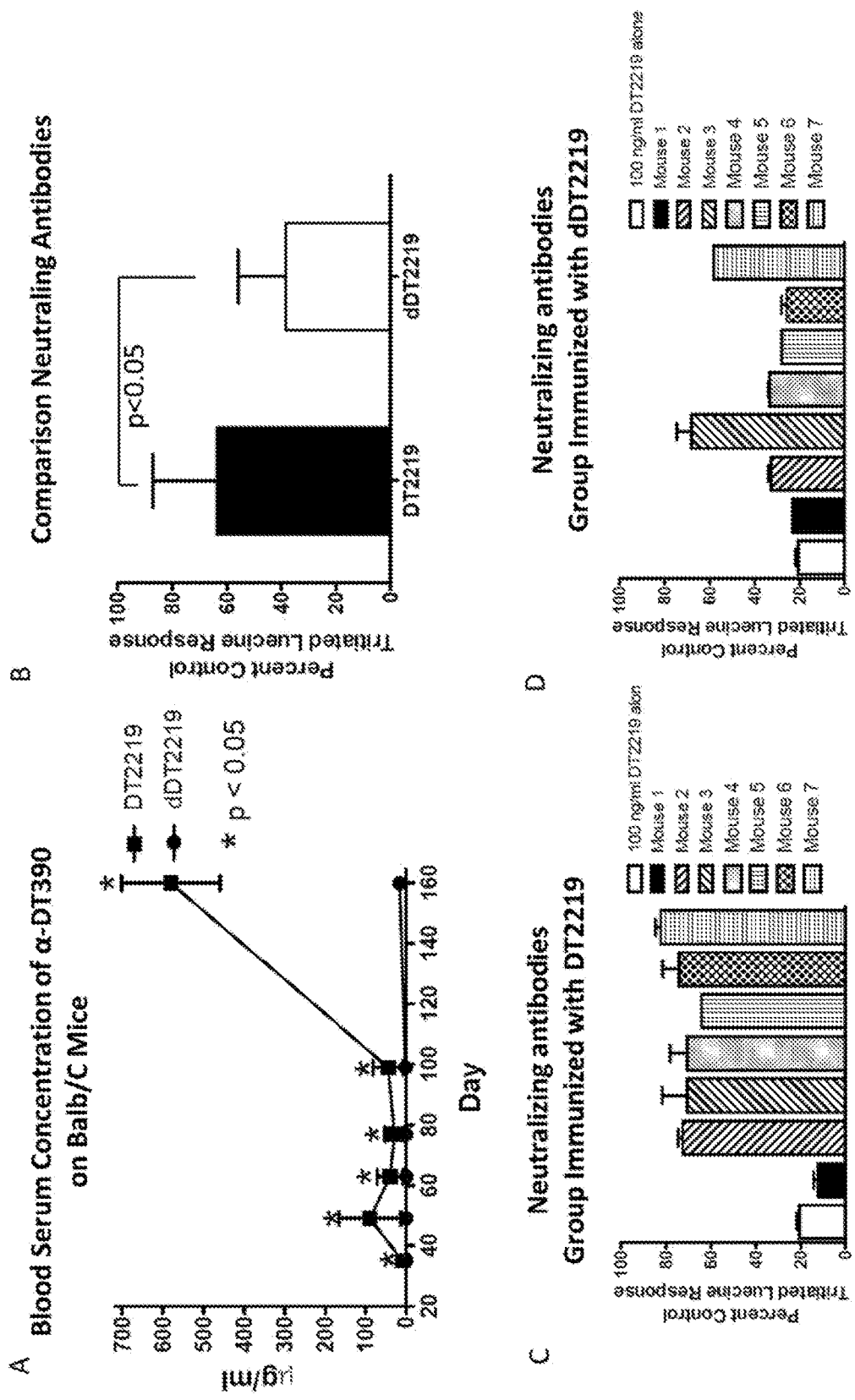

To evaluate whether neutralizing antibodies develop in the sera of immunized mice after repetitive exposure to dDT2219, BALB/c mice were divided into two groups of seven animals. Both groups were immunized simultaneously with either dDT2219 or DT2219 (control group). Both groups were treated with an equal concentration of dDT2219 or DT2219. In in all evaluated days, sera of the dDT2219 group showed a significantly lower (p<0.05) antibody induction, seen in an ELISA detecting α-DT390 (FIG. 15A). Even after four boosts with 1 μg of the respective drug at the end of the experiment, the dDT2219 group showed a significantly lower antibody induction.

In order to specify whether detected antibodies indeed neutralize dDT2219 or DT2219, a neutralization assay was performed using Raji targets and sera of both animal groups of day 160. A significantly lower amount of neutralizing antibodies (p<0.05) was found in the dDT2219 group (FIG. 15B) compared to the control group vaccinated with DT2219. Six of seven mice developed a high titer of neutralizing antibodies (FIG. 15C) after DT2219 vaccination, while only two of seven mice developed neutralizing antibodies in the dDT2219 group (FIG. 15D), (Table 1).

TABLE 1

| Animal experiment, neutralizing antibodies | | | | | | |
|---|---|---|---|---|---|---|
| | Day 35 | Day 49 | Day 63 | Day 77 | Day 99 | Day 160 |
| DT vaccination | | | | | | |
| M1 (ug/ml) | 0.00 | 0.00 | 0.30 | 0.30 | 0.29 | 24.50 |
| M2 (ug/ml) | 0.38 | 8.59 | 3.84 | 2.95 | 5.02 | 487.20 |
| M3 (ug/ml) | 1.04 | 8.28 | 5.52 | 4.40 | 8.79 | 1045.30 |
| M4 (ug/ml) | 48.36 | 548.72 | 229.65 | 169.84 | 267.31 | 789.20 |
| M5 (ug/ml) | 8.72 | 19.77 | 9.63 | 7.12 | 6.36 | 426.20 |
| M6 (ug/ml) | 4.34 | 26.37 | 16.84 | 12.51 | 13.57 | 650.70 |

TABLE 1-continued

| Animal experiment, neutralizing antibodies | | | | | | |
|---|---|---|---|---|---|---|
| | Day 35 | Day 49 | Day 63 | Day 77 | Day 99 | Day 160 |
| M7 (ug/ml) | 2.93 | 18.56 | 12.13 | 6.59 | 13.48 | 639.60 |
| Mean DT (ug/ml) | 9.40 | 90.04 | 39.70 | 29.10 | 44.97 | 580.39 |
| SD DT (ug/ml) | 17.44 | 202.45 | 83.94 | 62.18 | 98.15 | 318.76 |
| dDT vaccination | | | | | | |
| M1 (ug/ml) | 0.00 | 0.00 | 0.97 | 0.00 | 0.00 | 0.00 |
| M2 (ug/ml) | 0.00 | 0.31 | 0.00 | 1.65 | 8.15 | 6.20 |
| M3 (ug/ml) | 5.10 | 5.31 | 1.95 | 3.66 | 7.26 | 81.00 |
| M4 (ug/ml) | 0.00 | 0.27 | 0.00 | 0.18 | 0.00 | 8.10 |
| M5 (ug/ml) | 0.00 | 0.00 | 0.00 | 0.00 | 0.00 | 2.40 |
| M6 (ug/ml) | 0.00 | 0.00 | 0.00 | 0.00 | 0.00 | 3.30 |
| M7 (ug/ml) | 0.00 | 0.35 | 0.00 | 0.03 | 0.00 | 13.30 |
| Mean dDT (μg/ml) | 0.73 | 0.89 | 0.42 | 0.79 | 2.20 | 16.33 |
| SD dDT (μg/ml) | 1.93 | 2.0 | 0.8 | 1.4 | 3.8 | 28.8 |
| Comparison DT vs. dDT (p =) | 0.0001 | 0.0001 | 0.0001 | 0.0001 | 0.0001 | 0.0005 |

Abbreviations:
DT, Diphtheria toxin;
dDT, deimmunized Diphtheria toxin;
M, mouse;
SD, standard deviation Twenty-five patients with mature or precursor B-cell lymphoid malignancies expressing CD19 and/or CD22 were enrolled in a study to assess the safety of DT2219. All patients received a single course of DT2219. The most common adverse events (AE) including, weight gain, low albumin, transaminitis and fevers were transient grade 1-2 and occurred in patients in higher dose cohorts (≥40 μg/kg/day). Two subjects experienced DLT at dose levels 40 μg/kg and 60 μg/kg. Neutralizing antibodies were observed in 30% of patients after four courses of treatment and in all patients treated with at least 40 μg/kg (Bachanova et al., 2015. *Clin Cancer Res* 21:1267-1272).

Approaches to limit immunogenicity of DT2219 have been investigated, but none has proven to be a practical method for decreasing immune reactions to DT2219. Various approaches have included the use of polyethylene glycol (PEG) polymers or RNases, each of which can be conjugated to bioactive drugs, or co-administration with a B-cell depletive agents (e.g., rituximab).

Thus, this disclosure describes a deimmunized DT2219, dDT2219, as an exemplary targeted toxin with therapeutic activity. dDT2219 showed efficacy against B-cell malignancies, including two different Burkitt-lymphoma cell lines. No toxic effect for cell lines not expressing CD22 or CD19 was documented. The dDT2219 construct showed the same binding capacity to CLL as its parental form and a significantly lower induction of neutralizing antibodies in immunocompetent BALB/c mice. Since DT targeted toxin polypeptides and, in particular, DT2219 have provided promising results in induction of anti-cancer responses in vitro as well as in vivo, the deimmunized dDT2219 can provide anti-tumor therapy independent from limitation of anti-drug antibodies after multiple administrations and of vaccination status in a patient's records.

As noted above, the deimmunized targeted toxin can include a targeting domain that selectively binds to targets other than CD19 and/or CD22. Additional exemplary deimmunized bispecific targeted toxins have been produce and tested in an identical manner to dDT2219, as shown in Table 2.

TABLE 2

Additional exemplary deimmunized DT390 conjugates

| Construct | $IC_{50}$* | Immunogenic~ | Efficacy# | SEQ ID NO: |
|---|---|---|---|---|
| dDTEpCAMe23 | <10 nM | No | Yes | 9 |
| dDTEpCAM133 | <17 nM | No | Yes | 10 |
| dDTEGFATF | <10 nM | No | Yes | 11 |
| dDTROR1ATF | <19 nM | No | Yes | 12 |

*The concentration of drug that inhibits 50% drug activity as measured in in vitro tritiated thymidine uptake proliferation assay or tritiated leucine uptake protein synthesis assay.
~Immunogenicity studies described herein.
Efficacy measured in the efficacy xenomodels described herein.

dDTEpCAMe23 simultaneously targets EpCAM Epithelial cell adhesion molecule, a transmembrane glycoprotein mediating Ca2+-independent homotypic cell—cell adhesion in epithelia and e23 or HER2, a member of the human epidermal growth factor receptor (HER/EGFR/ERBB) family. dDTEpCAM133 simultaneously targets EpCAM and CD133, known as an established cancer stem cell marker. CD133, also known as prominin-1, is a glycoprotein that in humans is encoded by the PROM1 gene and a member of pentaspan transmembrane glycoproteins (5-transmembrane, 5-TM), which specifically localize to cellular protrusions. dDTEGFATF simultaneously targets EGFR and the amino terminal fragment (ATF) of urokinase (uPA). dDTROR1ATF simultaneously targets ATF and ROR1. ROR1 is a receptor tyrosine kinase modulating neurite growth. It is a type I membrane protein belonging to the ROR subfamily of cell surface receptors and is currently under investigation for its role in the metastasis of cancer cells.

In another aspect, this disclosure describes a method of killing a cell. Generally, the method includes contacting the cell with the deimmunized DT targeted toxin polypeptide described above, allowing the cell to internalize the deimmunized DT targeted toxin polypeptide, and allowing the deimmunized DT targeted toxin polypeptide to kill the cell. The method may be performed in vivo or in vitro.

In another aspect, this disclosure describes methods of treating a subject having a tumor. Generally, the method includes administering to the subject a deimmunized diphtheria toxin (dDT) targeted toxin compound in an amount effective to ameliorate at least one symptom or clinical sign of the tumor. "Treat" or variations thereof refer to reducing, limiting progression, ameliorating, or resolving, to any extent, the symptoms or signs related to a condition. As used herein, "ameliorate" refers to any reduction in the extent, severity, frequency, and/or likelihood of a symptom or clinical sign characteristic of a particular condition; "symptom" refers to any subjective evidence of disease or of a patient's condition; and "sign" or "clinical sign" refers to an objective physical finding relating to a particular condition capable of being found by one other than the patient.

A "treatment" may be therapeutic or prophylactic. "Therapeutic" and variations thereof refer to a treatment that ameliorates one or more existing symptoms or clinical signs associated with a condition. "Prophylactic" and variations thereof refer to a treatment that limits, to any extent, the development and/or appearance of a symptom or clinical sign of a condition. Generally, a "therapeutic" treatment is initiated after the condition manifests in a subject, while "prophylactic" treatment is initiated before a condition manifests in a subject. Thus, in certain embodiments, the method can involve prophylactic treatment of a subject at risk of developing a condition. "At risk" refers to a subject that may or may not actually possess the described risk. Thus, for example, a subject "at risk" for developing a specified condition is a subject that possesses one or more indicia of increased risk of having, or developing, the specified condition compared to individuals who lack the one or more indicia, regardless of the whether the subject manifests any symptom or clinical sign of having or developing the condition. Exemplary indicia of a condition can include, for example, genetic predisposition, ancestry, age, sex, geographical location, lifestyle, or medical history. Treatment may also be continued after symptoms have resolved, for example to prevent or delay their recurrence.

The dDT targeted toxin compound can be any embodiment of the dDT targeted toxin compound described above having a targeting domain that selectively binds to a target present on cells of the tumor.

In some cases, the tumor may be surgically resected or reduced through chemical (e.g., chemotherapeutic agents) and/or radiation therapy. In such embodiments, the dDT may be administered to the subject prior to, simultaneously with, or after the tumor is resected or reduced. Thus, in some embodiments, the dDT may be administered to the subject prior to, simultaneously with, or after a chemotherapeutic agent is administered to the subject.

The tumor may be a solid tumor or may be a liquid tumor. Accordingly, the dDT may be used to treat various forms of cancer including, for example, prostate cancer, lung cancer, colon cancer, rectum cancer, urinary bladder cancer, melanoma, kidney cancer, renal cancer, oral cavity cancer, pharynx cancer, pancreatic cancer, uterine cancer, thyroid cancer, skin cancer, head and neck cancer, cervical cancer, ovarian cancer, hematopoietic cancers and/or lymphatic cancers.

A "subject" may be any animal subject such as, for example, a mammalian subject (e.g., dog, cat, horse, cow, sheep, goat, monkey, primate, human, etc.). In some embodiments, the subject may be human, including both male and female subjects, and including neonatal, infant, juvenile, adolescent, adult and geriatric subjects.

Thus, in some embodiments, a targeting domain that includes a sufficient portion of epidermal growth factor (EGF) to selectively bind to epidermal growth factor receptor (EGFR) may be used to target a dDT targeted toxin compound to a tumor cell that expresses EGRF such as, for example, carcinomas of the prostate, pancreatic, breast, and/or lung.

In other embodiments, a targeting domain that includes an anti-CD19 and/or anti-CD 22 scFv may be used to target a dDT targeted toxin compound to a tumor cell that expressed CD19 and/or CD22 such as, for example, B cell malignancies such as non-Hodgkin's lymphoma (NHL), acute lymphoblastic leukemia (ALL), chronic lymphocytic leukemia (CLL), or Burkitt lymphoma.

A dDT targeted toxin described herein may be formulated with a pharmaceutically acceptable carrier. As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with a dDT targeted toxin without causing any undesirable biological effects or interacting in a deleterious manner with any of the other components of the pharmaceutical composition in which it is contained.

A dDT targeted toxin may therefore be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical composition can be administered to a mucosal surface, such as by administration to, for example, the nasal or respiratory mucosa (e.g., by spray or aerosol). A composition also can be administered via a sustained or delayed release.

Thus, a dDT targeted toxin may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a flavoring, a moisturizer, a thickener, and the like.

A formulation may be conveniently presented in unit dosage form and may be prepared by methods well known in the art of pharmacy. Methods of preparing a composition with a pharmaceutically acceptable carrier include the step of bringing a dDT targeted toxin into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

The amount of dDT targeted toxin administered can vary depending on various factors including, but not limited to, the specific dDT targeted toxin being used, the weight, physical condition, and/or age of the subject, and/or the route of administration. Thus, the absolute weight of dDT targeted toxin included in a given unit dosage form can vary widely, and depends upon factors such as the species, age, weight and physical condition of the subject, and/or the method of administration. Accordingly, it is not practical to set forth generally the amount that constitutes an amount of dDT targeted toxin effective for all possible applications. Those of ordinary skill in the art, however, can readily determine the appropriate amount with due consideration of such factors.

In some embodiments, the method can include administering sufficient dDT targeted toxin to provide a dose of, for example, from about 100 ng/kg to about 50 mg/kg to the subject, although in some embodiments the methods may be performed by administering dDT targeted toxin in a dose outside this range. In some of these embodiments, the method includes administering sufficient dDT targeted toxin to provide a dose of from about 10 µg/kg to about 5 mg/kg to the subject, for example, a dose of from about 100 µg/kg to about 1 mg/kg.

Alternatively, the dose may be calculated using actual body weight obtained just prior to the beginning of a treatment course. For the dosages calculated in this way, body surface area (m$^2$) is calculated prior to the beginning of the treatment course using the Dubois method: m$^2$=(wt kg$^{0.425}$×height cm$^{0.725}$)×0.007184.

In some embodiments, the method can include administering sufficient dDT targeted toxin to provide a dose of, for example, from about 0.01 mg/m$^2$ to about 10 mg/m$^2$.

In some embodiments, a dDT targeted toxin compound may be administered, for example, from a single dose to multiple doses per week, although in some embodiments the method can be performed by administering a dDT targeted toxin at a frequency outside this range. In certain embodiments, a dDT targeted toxin may be administered from about once per month to about five times per week.

In yet another aspect, this disclosure describes a method of deimmunizing a toxin. Generally, the method involves targeting hydrophilic amino acid residues located at surface positions of the toxin polypeptides that can be involved in generating anti-B cell responses, constructing a modified polypeptide that includes a substitution of one of the identified hydrophilic amino acid residues, screening the modified polypeptide for biological function of the native polypeptide, and screening the modified polypeptide for induction of antibodies. As used herein, "biological function," "biological activity," and variations thereof refer to a native biological function of the polypeptide. In some cases, however, the biological function (or biological activity, etc.) can refer to a particular function that is relevant to a therapeutic use of the polypeptide such as, for example, cytokine induction, cellular signaling, and the like.

The deimmunizing method was much less time consuming and more cost-effective than, for example, epitope mapping techniques. Using the known x-ray crystallographic structure of DT390, 24 potential amino acids (R, K, D, E, and Q) located in prominent positions on the molecular surface were selected in order to introduce point mutations at the selected sites. The DTEGF13 parental construct was mutated simultaneously with three site-specific PCR primers to generate triple mutants. Those that did not exhibit activity loss were further mutated, finally resulting in two constructs each with seven point mutations, but with minimal activity loss. Mutating DTEGF13 and expressing the product allows one to effectively screen the mutants for activity in vitro anti-carcinoma assays compared to the non-muted parental form.

The structure and mechanism of diphtheria toxin are well established. The point mutations were selected to be located well away from the catalytic active site. Moreover, in order to address whether point mutation removed T cell or B cell epitopes, two different strains of mice with different MHC haplotypes (H-2b and H-2d) were immunized. MHC molecules are supposed to load different regions of peptide fragments for presentation as T cell epitopes and T and B epitopes are not necessarily linked. The mutated drug (dDTEGF13; SEQ ID NO:8) was equally effective in reducing anti-toxin responses in both strains, indicating that B cell epitopes rather than T cell epitopes have been eliminated from DT.

In some cases, therefore, the dDT targeted toxin compound can exhibit at least 5% of the biological activity of the unmodified native diphtheria toxin such as, for example, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% of the biological activity of the unmodified native diphtheria toxin.

In some cases, the dDT targeted toxin compound can exhibit no more than 50% of the anti-toxin antibody induction of the unmodified native diphtheria toxin such as, for example, no more than 45%, no more than 40%, no more than 35%, no more than 30%, no more than 25%, no more than 20%, no more than 19%, no more than 18%, no more than 17%, no more than 16%, no more than 15%, no more than 14%, no more than 13%, no more than 12%, no more than 11%, no more than 10%, no more than 9%, no more than 8%, no more than 7%, no more than 6%, no more than 5%, no more than 4%, no more than 3%, no more than 2%, or no more than 1% of the anti-toxin antibody induction of the unmodified native diphtheria toxin.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Construction of dDTEGF13

The DTEGF13 coding region (SEQ ID NO:13) was originally synthesized using assembly PCR. In its final configuration, the coding region (from 5' end to 3' end) includes an NcoI restriction site, an ATG initiation codon, the first 389 amino acids of the DT molecule (DT390), the seven amino acid linker EASGGPE (SEQ ID NO:4), the coding regions for human EGF and IL-13 linked by a 20 amino acid segment of human muscle aldolase (hma), and an XhoI restriction site (FIG. 1A). The final 1755 bp NcoI/XhoI target gene was spliced into the pET21d expression vector under control of an isopropyl-b-D-thiogalactopyranoside (IPTG) inducible T7 promoter. DNA analysis was used to verify that the gene was in correct sequence (Biomedical Genomics Center, University of Minnesota). DTCD3CD3 was synthesized as a control by fusing two repeating scFvs recognizing human CD3epsilon to DT390 (Vallera et al., 2005, *Leuk Res* 29:331-341).

To create a deimmunized drug, DTEGF13 was mutated using the QuickChange Site-Directed Mutagenesis Kit (Stratagene. La Jolla, Calif.) and site specific mutations were confirmed by DNA sequencing.

Isolation of Inclusion Bodies, Refolding and Purification

These procedures were previously described (Stish et al., 2007, *Clin Cancer Res* 13:6486-6493). Plasmids were transformed into *E. coli* strain BL21(DE3) (Novagen, Madison, Wis.). Following overnight culture, bacteria were grown in Luria broth. Gene expression was induced with the addition of IPTG (FischerBiotech, Fair Lawn, N.J.). Two hours after induction, bacteria were harvested by centrifugation. Cell pellets were suspended and homogenized. Following sonication and centrifugation, the pellets were extracted and washed. Inclusion bodies were dissolved and protein refolded. Refolded proteins were purified by fast protein liquid chromatography ion exchange chromatography (Q SEPHAROSE Fast Flow, Sigma-Aldrich, St. Louis, Mo.) using a continuous gradient.

Antibodies and Cells

Anti-Ly5.2, a rat IgG2a from clone A20-1.7 was generously provided by Dr. Uli Hammerling, Sloan Kettering Cancer Research Center, New York, N.Y. Anti-Ly5.2 was used as a control since it recognized mouse CD45.1, a hematopoietic cell surface marker not expressed on human cells.

Human Cell Lines

The human prostate cancer cell line PC-3 (ATCC CRL-14435; Kaighn et al., 1979, *Invest Urol* 17:16-23), human colorectal cell line HT-29 (ATCC HTB-38; Fogh et al., 1977, *J Natl Cancer Inst* 59:221-226), the human pancreatic carcinoma MiaPaCa-2 (ATCC CRL-1420; Yunis et al. 1977, *Int J Cancer* 19:128-35), and the Burkitt's Lymphoma cell line Daudi (ATCC CCL-213; Klein et al., 1968, *Cancer Res* 28:1300-1310) were obtained from American Type Culture Collection (ATCC, Manassas, Va.). Cells were maintained in RPMI-1640 media (Cambrex, East Rutherford, N.J.) supplemented with 10% fetal bovine serum, 2 mmol/L L-glutamine, 100 units/mL penicillin, and 100 μg/mL streptomycin. All carcinoma cells were grown as monolayers and Daudi cells in suspension using culture flasks. Cell cultures were incubated in a humidified 37° C. atmosphere containing 5% $CO_2$. When adherent cells were 80-90% confluent, they were passaged using trypsin-EDTA for detachment. Only cells with viability >95%, as determined by TRYPAN blue exclusion, were used for experiments.

Proliferation Assay

To determine the effect of drug on tumor cells, cells ($2 \times 10^4$) were plated in a 96-well flat-bottom plate in RPMI supplemented with 10% fetal bovine serum, 2 mM L-glutamine, 100 U/ml penicillin, 100 μg/ml streptomycin. BLT in varying concentrations was added to triplicate wells containing cells (Tsai et al., 2011, *J Neurooncol* 103:255-266). The plates were incubated at 37° C., 5% $CO_2$ for 72 hours. Cells were then incubated with one μCi [methyl-$^3$H]-thymidine (GE Healthcare, UK) per well for eight hours and harvested onto glass fiber filters, washed, dried and counted for ten minutes in a standard scintillation counter. Data were analyzed using Prism 4 (GraphPad Software, Inc., San Diego, Calif.) and were presented as "percent control response" calculated by dividing the counts per minute (cpm) of untreated cells by the cpm of the immunotoxin-treated cells (×100).

Blocking studies were conducted to test specificity. Briefly, 1 nM, 10 nM, 100 nM, or 1000 nM EGF13 devoid of toxin were added to media containing 0.001 nM, 0.01 nM, 0.1 nM, 1 nM, 10 nM, or 100 nM DTEGF13 (Vallera et al., 2010, *Mol Cancer Ther* 9:1872-1883). Resulting mixtures were added to wells containing tumor cells and proliferation was measured by $^3$H-thymidine uptake as described. Data were presented as percent control response.

To detect neutralizing antibodies, 90% serum from immunized mice was added to cells treated with a known inhibitory concentration of DTEGF13 (1000 ng/ml). Proliferation assays were then carried out as described above.

Detection of Serum IgG Anti-Toxin Content Using ELISA Assay

The assay to detect IgG anti-toxin antibodies was previously reported (Vallera et al., 2009, *Leuk Res* 33:1233-1242). Briefly, immunocompetent normal BALB/c mice (NCI) were immunized with weekly injections of 0.25 μg non-mutated 2219KDEL or mutated 2219KDEL 7 mut. After five injections, serum was collected four days after the final injection. A standard ELISA assay was used in which recombinant DT390 was adhered to the plate. Test serum from the immunized mice was then added followed by the detection antibody, anti-mouse IgG peroxidase (Sigma-Aldrich, St. Louis, Mo.). Plates were developed with o-phenylenediamine dihydrochloride (Pierce Biotechnology, Rockford, Ill.) for 15 minutes at room temperature. The reaction was stopped with the addition of 2.5 M $H_2SO_4$. Absorbance was read at 490 nm and the final concentration was determined from a standard curve using highly purified anti-DT390. All samples and standards were tested in triplicate.

In Vivo Efficacy Studies

Male nu/nu mice were purchased from the National Cancer Institute, Frederick Cancer Research and Development Center, Animal Production Area and housed in an Association for Assessment and Accreditation of Laboratory Animal Care-accredited specific pathogen-free facility under the care of the Department of Research Animal Resources, University of Minnesota. Animal research protocols were approved by the University of Minnesota Institutional Animal Care and Use Committee. All animals were housed in microisolator cages to minimize the potential of contaminating virus transmission.

Our flank tumor model was previously reported (Stish et al., 2007, *Clin Canc Res* 13:6486-6493). This route of administration was chosen because the major point of this experiment was not to mimic a clinical protocol, but was to determine if deimmunized DTEGF13 was efficacious. Direct intratumoral administration circumvents the major problems of systemic administration. These include inefficient distribution to tumor site related to the distance traveled and unfavorable tumor vasculature dynamics (high interstitial pressures) (Jain R K 1989, *J Natl. Cancer Inst.* 81:570-576). Consequently, intratumoral therapy guarantees more consistent and reliable delivery of recombinant toxin fusion proteins to the targeted site with limited systemic exposure, which maximizes efficacy.

For induction of tumor, mice were injected in the left flank with $4 \times 10^6$ PC-3 cells suspended in 100 μL of a 1:1 RPMI/Matri-Gel mixture. Once palpable tumors had formed (day 15), mice were divided into groups and treated with multiple injections of DTEGF13 from day 15 to day 25. All drugs were administered by intratumoral injection using 3/10 cc syringes with 29 gauge needles. All treatments were given in a 100-μL volume of sterile PBS. Tumor size was measured using a digital caliper, and volume was determined as a product of length, width, and height.

Example 2

Construction of dDT2219

The dDT2219 coding region was synthesized using assembly PCR. The fully assembled coding region (from 5' end to 3' end) includes an NcoI restriction site, an ATG initiation codon, the first 390 amino acids of the mutated and deimmunized DT molecule (DT390), the seven amino acid linker EASGGPE (SEQ ID NO:4), the $V_L$ and $V_H$ regions of an anti-CD22 scFv, a GGGGS (SEQ ID NO:5) linker, the $V_L$ and $V_H$ regions of an anti-CD19 scFv, and a XhoI restriction site. The $V_L$ and $V_H$ gene of each scFv were joined by a linker (GSTSGSGKPGSGEGSTKG; SEQ ID NO:6) that was designated as aggregation reduced linker (ARL). The final 1755 bp NcoI/XhoI coding region was spliced into the pET21d expression vector under control of an isopropyl-b-D-thiogalactopyranoside (IPTG) inducible T7 promoter. DNA analysis was used to verify that the gene was in correct sequence (Biomedical Genomics Center, University of Minnesota, MN). To create a deimmunized drug, DT2219 was mutated using the QUICKCHANGE site-directed mutagenesis kit (Stratagene Corp., La Jolla Calif.) and site specific mutations were confirmed by DNA sequencing. The following amino acids were changed to deimmunize DT390: amino acid (aa) 125 changed from K to S; aa 173 R to A; aa 184 Q to S; aa 227 K to S; aa 245 Q to S; aa 292 E to S; and aa 385 K to G.

Inclusion Body Isolation, Refolding and Purification

*Escherichia coli* strain BL21 (DE3) (plasmid transfected) (Novagen, Inc., Madison, Wis., USA) was used for protein expression. Bacteria were cultured overnight in 800 ml Luria broth, containing 50 mg/ml carbenicillin. Expression was induced via addition of IPTG after the culture reached an optical density (OD) 600 of 0.65. Two hours after induction, grown bacteria were harvested and centrifuged. The cell pellet was homogenized in a solution buffer (50 mM tris, 50 mM NaCl, and 5 mM EDTA pH 8.0) and then sonicated and again centrifuged. Extraction of the pellet was performed using 0.3% sodium deoxycholate, 5% TRITON X-100, 10% glycerin, 50 mmol/L Tris, 50 mmol/L NaCl, 5 mmol/L EDTA (pH 8.0) and washed. Purification was described previously (Schmohl et al., 2015. *Targeted Oncology* 11(3):353-361; Schmohl et al., 2016. *Mol Ther* 24(7): 1312-1322). Homogenized inclusion bodies were dissolved and proteins refolded. Purification was performed using an ion exchange chromatography (Q SEPHAROSE Fast Flow, Sigma-Aldrich, St. Louis, Mo.) with a continuous gradient.

Tissue Cultures

The following cell lines were obtained from the American Type Culture Collection (ATCC, Manassas, Va.): Burkitt lymphoma cell line Daudi (ATCC CCL-213; Klein et al., 1968, *Cancer Res* 28:1300-1310) and Raji (ATCC CCL-86; Pulvertaft J V, 1964. *Lancet* 1:238-240), and human promyelocytic leukemia cell line HL-60 (ATCC CCL-240; Gallagher et al., 1979. *Blood* 54:713-733). T-cell leukemia HPB-MLT (Morikawa et al., 1978. *Int J Cancer* 21(2):166-170) was obtained from the German Collection of Microorganisms and Cell Cultures (Accession No. ACC 483). All cell lines were grown in suspension as previously described (Klein et al., 1968, *Cancer Res* 28:1300-1310). Cells were maintained in RPMI 1640 (supplemented with 10% fetal serum).

Proliferation Assay/Blocking Assay

In order to evaluate drug efficacy, $(2\times10^4)$ target cells were plated into a 96-well round bottom plate and suspended in RPMI supplemented with 10% fetal bovine serum, 2 mM L-glutamine, 100 U/ml penicillin, 100 μg/ml streptomycin. DT2219, dDT2219, or BIC3 (bivalent scFv construct consisting of the catalytic and translocation domains of diphtheria toxin and two anti-CD3 scFv; Vallera et al., 2005. *Leuk Res* 29:331-341) was added in different concentrations. Assays were performed in triplicates. For time-dependent assays, cells were incubated for 12 hours, 24 hours, or 36 hours. For regular proliferation assays, 72 hours of incubation was performed at 37° C., 5% $CO_2$. Cells were then incubated with one μCi [methyl-3H]-thymidine (GE Healthcare, UK) per well for eight hours and harvested onto glass fiber filters and washed. After a drying step, filters were counted for ten minutes in a standard scintillation counter. Data were analyzed using Prism 4 (GraphPad Software, Inc., La Jolla, Calif.) and were presented as "percent control response" calculated by dividing the counts per minute (CPM) of untreated cells by the CPM of the immunotoxin-treated cells (×100).

In order to assess specificity, blocking studies were performed. 100 nM, 200 nM, or 500 nM of 2219, the bispecific anti-CD19 and anti-CD22 scFv construct devoid of DT, was added to the respective amounts of either DT2219 or dDT2219 and incubated with target cells for 37° C. at 5% $CO_2$. After incubation $^3$H-thymidine uptake was measured as described above.

Patient Samples and Binding Assay

Twelve patient samples from CLL patients were collected at the University of Minnesota. Samples were cryoconserved and stored according to standard procedures until use. For evaluation of binding, $4\times10^5$ peripheral blood nuclear cells (PBMCs) of the respective samples were washed and incubated in 4° C. with no, 1 nM, 10 nM, 20 nM, 50 nM, or 100 nM of fluorescein isothiocyate (FITC)-labeled constructs: dDT2219, anti-EpCAM scFv (negative control), or DT2219. After 30 minutes of incubation at 4° C., cells were washed in 1×PBS and stained with APC Cy 7 conjugated anti-CD20 monoclonal antibody (mAb) (BioLegend, San Diego, Calif.), Pacific blue conjugated anti-CD5 mAb (BioLegend, San Diego, Calif.), or PE-CF592 conjugated anti-CD3 mAb (BD Biosciences, San Jose, Calif.) as previously described (Hayes, et al., 2010. *Leuk Res* 34:809-815). After incubation for 15 minutes, (4° C.), cells were washed with 1×PBS and fluorescence intensity was evaluated by FACS analysis using a LSRII flow cytometer (BD Biosciences, San Jose, Calif.).

Detecting Anti-Toxin Antibodies in Mice IgG anti-toxin antibodies were detected as previously described (Schmohl et al., 2015. *Toxins* 7:4067-4082). Briefly, immunocompetent normal BALB/c mice (NCI) were intraperitoneally immunized with non-mutated DT2219 (n=7 mice) or mutated DT2219 (dDT2219) (n=7 mice) (experiment registration number DAV529). Mice were immunized weekly for 12 weeks with 0.25 µg protein, followed by two weekly immunizations with 0.5 µg protein weekly, rested for six weeks, followed by weekly injections of 1 µg protein for three weeks. The experiment ended after 160 days. Blood was drawn on days 21, 35, 49, 63, 77, 99, and 160. A standard ELISA assay was used in which recombinant DT390 was adhered to the plate. Test serum from the immunized mice was then added followed by the detection antibody and anti-mouse IgG peroxidase (Sigma-Aldrich, St. Louis, Mo.). Plates were developed with o-phenylenediamine dihydrochloride (Thermo Fisher Scientific, Inc., Waltham, Mass.) for 15 minutes at room temperature. The reaction was stopped by adding 2.5 M $H_2SO_4$. Absorbance was read at 490 nm and the final concentration was determined from a standard curve using a mouse monoclonal antibody to diphtheria toxin ([11D9], Abcam Inc., Cambridge, Mass.). All samples and standards were tested in triplicates.

Detecting Neutralizing Antibodies in Mice

To detect neutralizing antibodies, 90% serum from immunized mice was added to cells, treated with a known inhibitory concentration of DT2219 and dDT2219 (1000 ng/ml). Proliferation assays were then carried out as described above. For detection of serum IgG anti-toxin content an ELISA Assay was used.

Statistical Analyses

Data are presented as mean+/−standard deviation. For evaluation of differences between the groups Student's t-test or one-way-ANOVA was used. Analysis and presentation of data was done with Graphpad prism 5 (GraphPad Software Inc., La Jolla, Calif., USA).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

```
                     Sequence Listing Free Text

SEQ ID NO: 3 (dDT2219)
GADDVVDSSK SFVMENFSSY HGTKPGYVDS IQKGIQKPKS GTQGNYDDDW KGFYSTDNKY
DAAGYSVDNE NPLSGKAGGV VKVTYPGLTN VLALKVDNAE TIKKELGLSL TEPLMEQVGT
EEFISRFGDG ASRVVLSLPF AEGSSSVEYI NNWEQAKALS VELEINFETR GKAGQDAMYE
YMASACAGNR VRRSVGSSLS CINLDWDVIR DKTKTKIESL KEHGPISNKM SESPNKTVSE
EKAKSYLEEF HQTALEHPEL SELKTVTGTN PVFAGANYAA WAVNVAQVID SSTADNLEKT
TAALSILPGI GSVMGIADGA VHHNTEEIVA QSIALSSLMV AQAIPLVGEL VDIGFAAYNF
VESIINLFQV VHNSYNRPAY SPGHGTQPFE ASGGPEDIQM TQTTSSLSAS LGDRVTISCR
ASQDISNYLN WYQQKPDGTV KLLIYYTSIL HSGVPSRFSG SGSGTDYSLT ISNLEQEDFA
TYFCQQGNTL PWTFGGGTKL EIKGSTSGSG KPGSGEGSTK GEVQLVESGG GLVKPGGSLK
LSCAASGFAF SIYDMSWVRQ TPEKRLEWVA YISSGGGTTY YPDTVKGRFT ISRDNAKNTL
YLQMSSLKSE DTAMYYCARH SGYGTHWGVL FAYWGQGTLV TVSAGGGGSD ILLTQTPASL
AVSLGQRATI SCKASQSVDY DGDSYLNWYQ QIPGQPPKLL IYDASNLVSG IPPRFSGSGS
GTDFTLNIHP VEKVDAATYH CQQSTEDPWT FGGGTKLEIK RGSTSGSGKP GSGEGSTKGQ
VQLQQSGAEL VRPGSSVKIS CKASGYAFSS YWMNWVKQRP GQGLEWIGQI WPGDGDTNYN
GKFKGKATLT ADESSSTAYM QLSSLASEDS AVYFCARRET TTVGRYYYAM DYWGQGTSVT
VSS

SEQ ID NO: 4
EASGGPE

SEQ ID NO: 5
GGGGS

SEQ ID NO: 6
GSTSGSGKPG SGEGSTKG

SEQ ID NO: 7 (dDT2219ARL)
GADDVVDSSK SFVMENFSSY HGTKPGYVDS IQKGIQKPKS GTQGNYDDDW KGFYSTDNKY
```

DAAGYSVDNE NPLSGKAGGV VKVTYPGLTN VLALKVDNAE TIKKELGLSL TEPLMEQVGT
EEFISRFGDG ASRVVLSLPF AEGSSSVEYI NNWEQAKALS VELEINFETR GKAGQDAMYE
YMASACAGNR VRRSVGSSLS CINLDWDVIR DKTKTKTIES KEHGPISNKM SESPNKTVSE
EKAKSYLEEF HQTALEHPEL SELKTVTGTN PVFAGANYAA WAVNVAQVID SSTADNLEKT
TAALSILPGI GSVMGIADGA VHHNTEEIVA QSIALSSLMV AQAIPLVGEL VDIGFAAYNF
VESIIINLFQV VHNSYNRPAY SPGHGTQPFE ASGGPEDIQM TQTTSSLSAS LGDRVTISCR
ASQDISNYLN WYQQKPDGTV KLLIYYTSIL HSGVPSRFSG SGSGTDYSLT ISNLEQEDFA
TYFCQQGNTL PWTFGGGTKL EIKGSTSGSG KPGSGEGSTK GEVQLVESGG GLVKPGGSLK
LSCAASGFAF SIYDMSWVRQ TPEKRLEWVA YISSGGGTTY YPDTVKGRFT ISRDNAKNTL
YLQMSSLKSE DTAMYYCARH SGYGTHWGVL FAYWGQGTLV TVSAGGGGSD ILLTQTPASL
AVSLGQRATI SCKASQSVDY DGDSYLNWYQ QIPGQPPKLL IYDASNLVSG IPPRFSGSGS
GTDFTLNIHP VEKVDAATYH CQQSTEDPWT FGGGTKLEIK RGSTSGSGKP GSGEGSTKGQ
VQLQQSGAEL VRPGSSVKIS CKASGYAFSS YWMNWVKQRP GQGLEWIGQI WPGDGDTNYN
GKFKGKATLT ADESSSTAYM QLSSLASEDS AVYFCARRET TTVGRYYYAM DYWGQGTSVT
VSS

SEQ ID NO: 8 (dDTEGF 13)
GADDVVDSSK SFVMENFSSY HGTKPGYVDS IQKGIQKPKS GTQGNYDDDW KGFYSTDNKY
DAAGYSVDNE NPLSGKAGGV VKVTYPGLTN VLALKVDNAE TIKKELGLSL TEPLMEQVGT
EEFISRFGDG ASRVVLSLPF AEGSSSVEYI NNWEQAKALS VELEINFETR GKAGQDAMYE
YMASACAGNR VRRSVGSSLS CINLDWDVIR DKTKTKIESL KEHGPISNKM SESPNKTVSE
EKAKSYLEEF HQTALEHPEL SELKTVTGTN PVFAGANYAA WAVNVAQVID SSTADNLEKT
TAALSILPGI GSVMGIADGA VHHNTEEIVA QSIALSSLMV AQAIPLVGEL VDIGFAAYNF
VESIIINLFQV VHNSYNRPAY SPGHGTQPFE ASGGPENSDS ECPLSHDGYC LHDGVCMYIE
ALDKYACNCV VGYIGERCQY RDLKWWELRP SGQAGAAASE SLFVSNHAYG PVPPSTALRE
LIEELVNITQ NQKAPLCNGS MVWSINLTAG MYCAALESLI NVSGCSAIEK TQRMLSGFCP
HKVSAGQFSS LHVRDTKIEV AQFVKDLLLH LKKLFREGRF N

SEQ ID NO: 9 (dDTEpCAMe23)
GADDVVDSSK SFVMENFSSY HGTKPGYVDS IQKGIQKPKS GTQGNYDDDW KGFYSTDNKY
DAAGYSVDNE NPLSGKAGGV VKVTYPGLTN VLALKVDNAE TIKKELGLSL TEPLMEQVGT
EEFISRFGDG ASRVVLSLPF AEGSSSVEYI NNWEQAKALS VELEINFETR GKAGQDAMYE
YMASACAGNR VRRSVGSSLS CINLDWDVIR DKTKTKIESL KEHGPISNKM SESPNKTVSE
EKAKSYLEEF HQTALEHPEL SELKTVTGTN PVFAGANYAA WAVNVAQVID SSTADNLEKT
TAALSILPGI GSVMGIADGA VHHNTEEIVA QSIALSSLMV AQAIPLVGEL VDIGFAAYNF
VESIIINLFQV VHNSYNRPAY SPGHGTQPFE ASGGPEDIQM TQSPSSLSAS VGDRVTITCR
STKSLLHSNG ITYLYWYQQK PGKAPKLLIY QMSNLASGVP SRFSSSGSGT DFTLTISSLQ
PEDFATYYCA QNLEIPRTFG QGTKVELKRA TPSHNSHQVP SAGGPTANSG TSGEVQLVQS
GPGLVQPGGS VRISCAASGY TFTNYGMNWV KQAPGKGLEW MGWINTYTGE STYADSFKGR
FTFSLDTSAS AAYLQINSLR AEDTAVYYCA RFAIKGDYWG QGTLLTVSSP SGQAGAAASE
SLFVSNHAYD VQLTQSPAIL SASPGEKVTM TCRATPSVSY MHWYQQKPGS SPKPWIYTTS
NLASGVPARF SGGGSGTSYS LTVSRVEAED AATYYCQQWS RSPPTFGGGS KLEIKGSTSG
SGKSSEGKGV QLQESGPEVV KPGGSMKISC KTSGYSFTGH TMNWVKQSHG KNLEWIGLIN
PYNGDTNYNQ KFKGKATFTV DKSSSTAYME LLSLTSEDSA VYYCARRVTD WYFDVWGAGT
TVTVS

SEQ ID NO: 10 (dDTEpCAM133)
GADDVVDSSK SFVMENFSSY HGTKPGYVDS IQKGIQKPKS GTQGNYDDDW KGFYSTDNKY
DAAGYSVDNE NPLSGKAGGV VKVTYPGLTN VLALKVDNAE TIKKELGLSL TEPLMEQVGT
EEFISRFGDG ASRVVLSLPF AEGSSSVEYI NNWEQAKALS VELEINFETR GKAGQDAMYE
YMASACAGNR VRRSVGSSLS CINLDWDVIR DKTKTKIESL KEHGPISNKM SESPNKTVSE
EKAKSYLEEF HQTALEHPEL SELKTVTGTN PVFAGANYAA WAVNVAQVID SSTADNLEKT
TAALSILPGI GSVMGIADGA VHHNTEEIVA QSIALSSLMV AQAIPLVGEL VDIGFAAYNF
VESIIINLFQV VHNSYNRPAY SPGHGTQPFE ASGGPEDIQM TQSPSSLSAS VGDRVTITCR
STKSLLHSNG ITYLYWYQQK PGKAPKLLIY QMSNLASGVP SRFSSSGSGT DFTLTISSLQ
PEDFATYYCA QNLEIPRTFG QGTKVELKRA TPSHNSHQVP SAGGPTANSG TSGEVQLVQS
GPGLVQPGGS VRISCAASGY TFTNYGMNWV KQAPGKGLEW MGWINTYTGE STYADSFKGR
FTFSLDTSAS AAYLQINSLR AEDTAVYYCA RFAIKGDYWG QGTLLTVSSE PKSSDKTHTS
PPSPDIVLSQ SPAIMSASPG EKVTISCSAS SSVSYMYWYQ QKPGSSPKPW IYRTSNLASG
VPARFSGSGS GTSYSLTISS MEAEDAATYY CQQYHSYPPT FGAGTKLELK SSGGGGSGGG
GGGSSRSSLE VKLVESGPEL KKPGETVKIS CKASGYTFTD YSMHWVNQAP GKGLKWMGWI
NTETGEPSYA DDFKGRFAFS LETSASTAYL QINNLKNEDT ATYFCATDYG DYFDYWGQGT
TLTVSSAKTT PPSVTS

SEQ ID NO: 11 (dDTEGFATF)
GADDVVDSSK SFVMENFSSY HGTKPGYVDS IQKGIQKPKS GTQGNYDDDW KGFYSTDNKY
DAAGYSVDNE NPLSGKAGGV VKVTYPGLTN VLALKVDNAE TIKKELGLSL TEPLMEQVGT
EEFISRFGDG ASRVVLSLPF AEGSSSVEYI NNWEQAKALS VELEINFETR GKAGQDAMYE
YMASACAGNR VRRSVGSSLS CINLDWDVIR DKTKTKIESL KEHGPISNKM SESPNKTVSE
EKAKSYLEEF HQTALEHPEL SELKTVTGTN PVFAGANYAA WAVNVAQVID SSTADNLEKT
TAALSILPGI GSVMGIADGA VHHNTEEIVA QSIALSSLMV AQAIPLVGEL VDIGFAAYNF
VESIIINLFQV VHNSYNRPAY SPGHGTQPFE ASGGPENSDS ECPLSHDGYC LHDGVCMYIE
ALDKYACNCV VGYIGERCQY RDLKWWELRP SGQAGAAASE SLFVSNHAYS NELHQVPSNC
DCLNGGTCVS NKYFSNIHWC NCPKKFGGQH CEIDKSKTCY EGNGHFYRGK ASTDTMGRPC
LPWNSATVLQ QTYHAHRSDA LQLGLGKHNY CRNPDNRRRP WCYVQVGLKP LVQECMVHDC
ADGK

Sequence Listing Free Text

SEQ ID NO: 12 (dDTROR1ATF)
GADDVVDSSK SFVMENFSSY HGTKPGYVDS IQKGIQKPKS GTQGNYDDDW KGFYSTDNKY
DAAGYSVDNE NPLSGKAGGV VKVTYPGLTN VLALKVDNAE TIKKELGLSL TEPLMEQVGT
EEFISRFGDG ASRVVLSLPF AEGSSSVEYI NNWEQAKALS VELEINFETR GKAGQDAMYE
YMASACAGNR VRRSVGSSLS CINLDWDVIR DKTKTKIESL KEHGPISNKM SESPNKTVSE
EKAKSYLEEF HQTALEHPEL SELKTVTGTN PVFAGANYAA WAVNVAQVID SSTADNLEKT
TAALSILPGI GSVMGIADGA VHHNTEEIVA QSIALSSLMV AQAIPLVGEL VDIGFAAYNF
VESIINLFQV VHNSYNRPAY SPGHGTQPFE ASGGPEQVQL QQSGAELVRP GASVTLSCKA
SGYTFSDYEM HWVIQTPVHG LEWIGAIDPE TGGTAYNQKF KGKAILTADK SSSTAYMELR
SLTSEDSAVY YCTGYYDYDS FTYWGQGTLV TVSAGGGGSG GGGSGGGGSD IVMTQSQKIM
STTVGDRVSI TCKASQNVDA AVAWYQQKPG QSPKLLIYSA SNRYTGVPDR FTGSGSGTDF
TLTISNMQSE DLADYFCQQY DIYPYTFGGG TKLEIKPSGQ AGAAASESLF VSNHAYSNEL
HQVPSNCDCL NGGTCVSNKY FSNIHWCNCP KKFGGQHCEI DKSKTCYEGN GHFYRGKAST
DTMGRPCLPW SATVLQQTYH AHRSDALQLG LGKHNYCRNP DNRRRPWCYV QVGLKPLVQE
CMVHDCADGK

SEQ ID NO: 13 (dDTEGF13 Coding Sequence)
GGCGCTGATG ATGTTGTTGA TTCTTCTAAA TCTTTTGTGA TGGAAAACTT TTCTTCGTAC
CACGGGACTA AACCTGGTTA TGTAGATTCC ATTCAAAAAG GTATACAAAA GCCAAAATCT
GGTACACAAG GAAATTATGA CGATGATTGG AAAGGGTTTT ATAGTACCGA CAATAAATAC
GACGCTGCGG GATACTCTGT AGATAATGAA AACCCGCTCT CTGGAAAAGC TGGAGGCGTG
GTCAAAGTGA CGTATCCAGG ACTGACGAAC GTTCTCGCAC TAAAAGTGGA TAATGCCGAA
ACTATTAAGA AAGAGTTAGG TTTAAGTCTC ACTGAACCGT TGATGGAGCA AGTCGGAACG
GAAGAGTTTA TCTCAAGGTT CGGTGATGGT GCTTCGCGTG TAGTGCTCAG CCTTCCCTTC
GCTGAGGGGA GTTCTAGCGT TGAATATATT AATAACTGGG AACAGGCGAA AGCGTTAAGC
GTAGAACTTG AGATTAATTT TGAAACCCGT GGAAAAGCTG GCCAAGATGC GATGTATGAG
TATATGGCTT CAGCCTGTGC AGGAAATCGT GTCAGGCGAT CAGTAGGTAG CTCATTGTCA
TGCATAAATC TTGATTGGGA TGTCATAAGG GATAAAACTA AGACAAAGAT AGAGTCTTTG
AAAGAGCATG GCCCTATCTC AAATAAAATG AGCGAAAGTC CCAATAAAAC AGTATCTGAG
GAAAAAGCTA AATCATACCT AGAAGAATTC ATCAAACGG CATTAGAGCA TCCTGAATTG
TCAGAACTTA AAACCGTTAC TGGGACCAAT CCTGTATTCG CTGGGGCTAA CTATGCGGCG
TGGGCAGTAA ACGTTGCGCA AGTTATCGAT AGCTCAACAG CTGATAATTT GGAAAAGACA
ACTGCTGCTC TTTCGATACT TCCTGGTATC GGTAGCGTAA TGGGCATTGC AGACGGTGCC
GTTCACCACA ATACAGAAGA GATAGTGGCA AATCAATAG CTTTATCGTC TTTAATGGTT
GCTCAAGCTA TTCCATTGGT AGGAGAGCTA GTTGATATTG GTTTCGCTGC ATATAATTTT
GTAGAGAGTA TTATCAATTT ATTTCAAGTA GTTCATAATT CGTATAATCG TCCCGCGTAT
TCTCCGGGGC ATGGAACGCA ACCATTTGAA GCTTCCGGAG GTCCCGAGAA CAGCGACAGC
GAATGTCCGC TGAGCCACGA CGGTTACTGT CTGCACGACG GTGTTTGTAT GTACATCGAA
GCTCTAGACA ATACGCTTG TAACTGTGTT GTTGGTTACA TCGGTGAACG CTGTCAGTAC
CGCGACCTGA ATGGTGGGA ACTGCGCCCG TCTGGTCAGG CTGGTGCTGC TGCTAGCGAA
TCTCTGTTCG TTTCTAACCA CGCTTACGGG CCTGTGCCTC CCTCTACAGC CCTCAGGGAG
CTCATTGAGG AGCTGGTCAA CATCACCCAG AACCAGAAGG CTCCGCTCTG CAATGGCAGC
ATGGTATGGA GCATCAACCT GACAGCTGGC ATGTACTGTG CAGCCCTGGA ATCCCTGATC
AACGTGTCAG GCTGCAGTGC CATCGAGAAG ACCCAGAGGA TGCTGAGCGG ATTCTGCCCG
CACAAGGTCT CAGCTGGGCA GTTTTCCAGC TTGCATGTCC GAGACACCAA AATCGAGGTG
GCCCAGTTTG TAAAGGACCT GCTCTTACAT TTAAAGAAAC TTTTTCGCGA GGGACGGTTC
APC

What is claimed is:

1. A polypeptide comprising:
   a diphtheria toxin (DT) domain comprising a variant of DT390, the variant of DT390 comprising:
   the DT catalytic site;
   the K125S, R173A and Q245S amino acid substitutions in the amino acid sequence of SEQ ID NO: 1; and
   at least one targeting domain that selectively binds to a target cell.

2. The polypeptide of claim 1, wherein the polypeptide exhibits measurable diphtheria toxin toxicity.

3. The polypeptide of claim 1, wherein the target cell is a tumor cell and the targeting domain binds to a receptor on the tumor cell.

4. The polypeptide of claim 1, wherein the targeting domain comprises an epidermal growth factor (EGF) polypeptide that selectively binds to epidermal growth factor receptor (EGFR).

5. The polypeptide of claim 1, wherein the targeting domain comprises IL-13 polypeptide that selectively binds to IL-13 receptor.

6. The polypeptide of claim 1, wherein the targeting domain comprises a polypeptide that selectively binds to CD22.

7. The polypeptide of claim 1, wherein the targeting domain comprises a polypeptide that selectively binds to CD19.

8. The polypeptide of claim 1, wherein the polypeptide comprises at least two targeting domains.

9. The polypeptide of claim 8, wherein a first targeting domain comprises IL-13 polypeptide and a second targeting domain comprises an epidermal growth factor (EGF) polypeptide.

10. The polypeptide of claim 8, wherein a first targeting domain comprises a polypeptide that selectively binds CD19 and a second targeting domain comprises a polypeptide that selectively binds CD22.

11. The polypeptide of claim 1, wherein the variant of DT390 further comprises the K385G and E292S amino acid substitutions in the amino acid sequence of SEQ ID NO: 1.

12. The polypeptide of claim 11, wherein the variant of DT390 further comprises the Q184S and K227S amino acid substitutions in the amino acid sequence of SEQ ID NO: 1.

13. A method of killing a target cell that expresses a receptor, the method comprising:
   providing a polypeptide comprising:
   a diphtheria toxin (DT) domain comprising a variant of DT390, the variant of DT390 comprising:

the DT catalytic site;

the K125S, R173A and Q245S amino acid substitutions in the amino acid sequence of SEQ ID NO: 1; and at least one targeting domain that selectively binds to the receptor expressed on the target cell;

contacting the target cell with the polypeptide under conditions that allow the target cell to internalize the polypeptide; and allowing the polypeptide to kill the target cell.

14. The method of claim 13, wherein the target cell is present in vitro.

15. The method of claim 13, wherein the target cell is an in vivo target cell.

16. The method of claim 13, wherein the at least one targeting domain selectively binds to Her2, ROR1, CD19, CD22, CD133, CD20, CD33, CD52, EpCAM, CEA, UPA, or VEGFR.

17. The method of claim 13, wherein the polypeptide is administered prior to, simultaneously with, or following administration of a chemotherapeutic drug.

18. A method of treating a subject having a tumor, the method comprising administering to the subject an amount of the polypeptide of claim 1 effective to ameliorate at least one symptom or clinical sign of the tumor, wherein the at least one targeting domain selectively binds to a target receptor expressed on cells of the tumor.

19. The method of claim 18, wherein the target receptor is epidermal growth factor receptor (EGFR).

20. A method of producing a deimmunized diphtheria toxin polypeptide which comprises the diphtheria toxin catalytic site, the method comprising:

modifying a wild-type diphtheria toxin (DT) polypeptide by including the K125S, R173A and Q245S amino acid substitutions in the amino acid sequence of SEQ ID NO: 1 to produce a modified DT polypeptide;

screening the modified DT polypeptide for toxicity of the wild-type DT polypeptide;

screening the modified DT polypeptide for induction of anti-DT toxin antibodies; and obtaining the modified DT polypeptide exhibiting measurable DT toxicity and reduced induction of anti-DT toxin antibodies compared to the wild-type DT to produce the deimmunized diphtheria toxin polypeptide.

21. The method of claim 20, wherein the modifying further comprises including the K385G and E292S amino acid substitutions in the amino acid sequence of SEQ ID NO: 1.

22. The method of claim 21, wherein the modifying further comprises including the Q184S and K227S amino acid substitutions in the amino acid sequence of SEQ ID NO: 1.

* * * * *

SEQUENCE LISTING

<160> NUMBER OF SEQ ID NOS: 13

<210> SEQ ID NO 1
<211> LENGTH: 389
<212> TYPE: PRT
<213> ORGANISM: Artificial
<220> FEATURE:
<223> OTHER INFORMATION: Polypeptide

<400> SEQUENCE: 1

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
 65                  70                  75                  80

Val Lys Val Thr Tyr Pro Gly Leu Thr Asn Val Leu Ala Leu Lys Val
                 85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Ser Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Ala Gly Gln Asp
                165                 170                 175

Ala Met Tyr Glu Tyr Met Ala Ser Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Ser Asn Lys Met Ser Glu Ser Pro Asn Lys Thr Val Ser Glu
225                 230                 235                 240

Glu Lys Ala Lys Ser Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Ser Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Gly Thr Gln Pro Phe
385

<210> SEQ ID NO 2
<211> LENGTH: 387
<212> TYPE: PRT
<213> ORGANISM: Artificial
<220> FEATURE:
<223> OTHER INFORMATION: Polypeptide

<400> SEQUENCE: 2

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

```
Gln Lys Gly Ile Gln Lys Pro Lys Ser Gly Thr Gln Gly Asn Tyr Asp
             35                  40                  45

Asp Asp Trp Lys Gly Phe Tyr Ser Thr Asp Asn Lys Tyr Asp Ala Ala
 50                  55                  60

Gly Tyr Ser Val Asp Asn Glu Asn Pro Leu Ser Gly Lys Ala Gly Gly
 65                  70                  75                  80

Val Val Lys Val Thr Tyr Pro Gly Leu Thr Lys Val Leu Ala Leu Lys
                 85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Phe Ile Lys Arg Phe
            115                 120                 125

Gly Asp Gly Ala Ser Arg Val Val Leu Ser Leu Pro Phe Ala Glu Gly
130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr
385
```

<210> SEQ ID NO 3
<211> LENGTH: 903
<212> TYPE: PRT
<213> ORGANISM: Artificial
<220> FEATURE:
<223> OTHER INFORMATION: Polypeptide

<400> SEQUENCE: 3

-continued

```
Gly Ala Asp Asp Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
            35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Lys Ala Gly Gly Val
65                  70                  75                  80

Val Lys Val Thr Tyr Pro Gly Leu Thr Asn Val Leu Ala Leu Lys Val
                85                  90                  95

Asp Asn Ala Glu Thr Ile Lys Lys Glu Leu Gly Leu Ser Leu Thr Glu
                100                 105                 110

Pro Leu Met Glu Gln Val Gly Thr Glu Glu Phe Ile Ser Arg Phe Gly
            115                 120                 125

Asp Gly Ala Ser Arg Val Val Leu Ser Leu Pro Phe Ala Glu Gly Ser
        130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Ala Gly Gln Asp
                165                 170                 175

Ala Met Tyr Glu Tyr Met Ala Ser Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Ser Asn Lys Met Ser Glu Ser Pro Asn Lys Thr Val Ser Glu
225                 230                 235                 240

Glu Lys Ala Lys Ser Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Ser Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Gly Thr Gln Pro Phe Glu Ala Ser Gly Gly Pro Glu Asp Ile Gln Met
385                 390                 395                 400

Thr Gln Thr Thr Ser Ser Leu Ser Ala Ser Leu Gly Asp Arg Val Thr
                405                 410                 415

Ile Ser Cys Arg Ala Ser Gln Asp Ile Ser Asn Tyr Leu Asn Trp Tyr
```

```
                420                 425                 430
Gln Gln Lys Pro Asp Gly Thr Val Lys Leu Leu Ile Tyr Tyr Thr Ser
            435                 440                 445
Ile Leu His Ser Gly Val Pro Ser Arg Phe Ser Gly Ser Gly Ser Gly
            450                 455                 460
Thr Asp Tyr Ser Leu Thr Ile Ser Asn Leu Glu Gln Glu Asp Phe Ala
465                 470                 475                 480
Thr Tyr Phe Cys Gln Gln Gly Asn Thr Leu Pro Trp Thr Phe Gly Gly
                485                 490                 495
Gly Thr Lys Leu Glu Ile Lys Gly Ser Thr Ser Gly Ser Gly Lys Pro
            500                 505                 510
Gly Ser Gly Glu Gly Ser Thr Lys Gly Glu Val Gln Leu Val Glu Ser
            515                 520                 525
Gly Gly Gly Leu Val Lys Pro Gly Gly Ser Leu Lys Leu Ser Cys Ala
            530                 535                 540
Ala Ser Gly Phe Ala Phe Ser Ile Tyr Asp Met Ser Trp Val Arg Gln
545                 550                 555                 560
Thr Pro Glu Lys Arg Leu Glu Trp Val Ala Tyr Ile Ser Ser Gly Gly
                565                 570                 575
Gly Thr Thr Tyr Tyr Pro Asp Thr Val Lys Gly Arg Phe Thr Ile Ser
                580                 585                 590
Arg Asp Asn Ala Lys Asn Thr Leu Tyr Leu Gln Met Ser Ser Leu Lys
            595                 600                 605
Ser Glu Asp Thr Ala Met Tyr Tyr Cys Ala Arg His Ser Gly Tyr Gly
            610                 615                 620
Thr His Trp Gly Val Leu Phe Ala Tyr Trp Gly Gln Gly Thr Leu Val
625                 630                 635                 640
Thr Val Ser Ala Gly Gly Gly Gly Ser Asp Ile Leu Leu Thr Gln Thr
                645                 650                 655
Pro Ala Ser Leu Ala Val Ser Leu Gly Gln Arg Ala Thr Ile Ser Cys
            660                 665                 670
Lys Ala Ser Gln Ser Val Asp Tyr Asp Gly Asp Ser Tyr Leu Asn Trp
            675                 680                 685
Tyr Gln Gln Ile Pro Gly Gln Pro Pro Lys Leu Leu Ile Tyr Asp Ala
            690                 695                 700
Ser Asn Leu Val Ser Gly Ile Pro Pro Arg Phe Ser Gly Ser Gly Ser
705                 710                 715                 720
Gly Thr Asp Phe Thr Leu Asn Ile His Pro Val Glu Lys Val Asp Ala
                725                 730                 735
Ala Thr Tyr His Cys Gln Gln Ser Thr Glu Asp Pro Trp Thr Phe Gly
                740                 745                 750
Gly Gly Thr Lys Leu Glu Ile Lys Arg Gly Ser Thr Ser Gly Ser Gly
            755                 760                 765
Lys Pro Gly Ser Gly Glu Gly Ser Thr Lys Gly Gln Val Gln Leu Gln
            770                 775                 780
Gln Ser Gly Ala Glu Leu Val Arg Pro Gly Ser Ser Val Lys Ile Ser
785                 790                 795                 800
Cys Lys Ala Ser Gly Tyr Ala Phe Ser Ser Tyr Trp Met Asn Trp Val
                805                 810                 815
Lys Gln Arg Pro Gly Gln Gly Leu Glu Trp Ile Gly Gln Ile Trp Pro
            820                 825                 830
Gly Asp Gly Asp Thr Asn Tyr Asn Gly Lys Phe Lys Gly Lys Ala Thr
            835                 840                 845
```

```
Leu Thr Ala Asp Glu Ser Ser Thr Ala Tyr Met Gln Leu Ser Ser
        850                 855                 860

Leu Ala Ser Glu Asp Ser Ala Val Tyr Phe Cys Ala Arg Arg Glu Thr
865                 870                 875                 880

Thr Thr Val Gly Arg Tyr Tyr Tyr Ala Met Asp Tyr Trp Gly Gln Gly
                885                 890                 895

Thr Ser Val Thr Val Ser Ser
            900

<210> SEQ ID NO 4
<211> LENGTH: 7
<212> TYPE: PRT
<213> ORGANISM: Artificial
<220> FEATURE:
<223> OTHER INFORMATION: Polypeptide

<400> SEQUENCE: 4

Glu Ala Ser Gly Gly Pro Glu
1               5

<210> SEQ ID NO 5
<211> LENGTH: 5
<212> TYPE: PRT
<213> ORGANISM: Artificial
<220> FEATURE:
<223> OTHER INFORMATION: Polypeptide

<400> SEQUENCE: 5

Gly Gly Gly Gly Ser
1               5

<210> SEQ ID NO 6
<211> LENGTH: 18
<212> TYPE: PRT
<213> ORGANISM: Artificial
<220> FEATURE:
<223> OTHER INFORMATION: Polypeptide

<400> SEQUENCE: 6

Gly Ser Thr Ser Gly Ser Gly Lys Pro Gly Ser Gly Glu Gly Ser Thr
1               5                   10                  15

Lys Gly

<210> SEQ ID NO 7
<211> LENGTH: 903
<212> TYPE: PRT
<213> ORGANISM: Artificial
<220> FEATURE:
<223> OTHER INFORMATION: Polypeptide

<400> SEQUENCE: 7

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80
```

```
Val Lys Val Thr Tyr Pro Gly Leu Thr Asn Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Ser Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Ala Gly Gln Asp
                165                 170                 175

Ala Met Tyr Glu Tyr Met Ala Ser Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Ser Asn Lys Met Ser Glu Ser Pro Asn Lys Thr Val Ser Glu
225                 230                 235                 240

Glu Lys Ala Lys Ser Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Ser Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Gly Thr Gln Pro Phe Glu Ala Ser Gly Gly Pro Glu Asp Ile Gln Met
385                 390                 395                 400

Thr Gln Thr Thr Ser Ser Leu Ser Ala Ser Leu Gly Asp Arg Val Thr
                405                 410                 415

Ile Ser Cys Arg Ala Ser Gln Asp Ile Ser Asn Tyr Leu Asn Trp Tyr
            420                 425                 430

Gln Gln Lys Pro Asp Gly Thr Val Lys Leu Leu Ile Tyr Tyr Thr Ser
        435                 440                 445

Ile Leu His Ser Gly Val Pro Ser Arg Phe Ser Gly Ser Gly Ser Gly
    450                 455                 460

Thr Asp Tyr Ser Leu Thr Ile Ser Asn Leu Glu Gln Glu Asp Phe Ala
465                 470                 475                 480

Thr Tyr Phe Cys Gln Gln Gly Asn Thr Leu Pro Trp Thr Phe Gly Gly
                485                 490                 495

Gly Thr Lys Leu Glu Ile Lys Gly Ser Thr Ser Gly Ser Gly Lys Pro
```

```
            500                 505                 510
Gly Ser Gly Glu Gly Ser Thr Lys Gly Glu Val Gln Leu Val Glu Ser
            515                 520                 525
Gly Gly Gly Leu Val Lys Pro Gly Gly Ser Leu Lys Leu Ser Cys Ala
            530                 535                 540
Ala Ser Gly Phe Ala Phe Ser Ile Tyr Asp Met Ser Trp Val Arg Gln
545                 550                 555                 560
Thr Pro Glu Lys Arg Leu Glu Trp Val Ala Tyr Ile Ser Ser Gly Gly
                565                 570                 575
Gly Thr Thr Tyr Tyr Pro Asp Thr Val Lys Gly Arg Phe Thr Ile Ser
                580                 585                 590
Arg Asp Asn Ala Lys Asn Thr Leu Tyr Leu Gln Met Ser Ser Leu Lys
                595                 600                 605
Ser Glu Asp Thr Ala Met Tyr Tyr Cys Ala Arg His Ser Gly Tyr Gly
            610                 615                 620
Thr His Trp Gly Val Leu Phe Ala Tyr Trp Gly Gln Gly Thr Leu Val
625                 630                 635                 640
Thr Val Ser Ala Gly Gly Gly Ser Asp Ile Leu Leu Thr Gln Thr
                645                 650                 655
Pro Ala Ser Leu Ala Val Ser Leu Gly Gln Arg Ala Thr Ile Ser Cys
                660                 665                 670
Lys Ala Ser Gln Ser Val Asp Tyr Asp Gly Asp Ser Tyr Leu Asn Trp
            675                 680                 685
Tyr Gln Gln Ile Pro Gly Gln Pro Pro Lys Leu Leu Ile Tyr Asp Ala
        690                 695                 700
Ser Asn Leu Val Ser Gly Ile Pro Pro Arg Phe Ser Gly Ser Gly Ser
705                 710                 715                 720
Gly Thr Asp Phe Thr Leu Asn Ile His Pro Val Glu Lys Val Asp Ala
                725                 730                 735
Ala Thr Tyr His Cys Gln Gln Ser Thr Glu Asp Pro Trp Thr Phe Gly
                740                 745                 750
Gly Gly Thr Lys Leu Glu Ile Lys Arg Gly Ser Thr Ser Gly Ser Gly
            755                 760                 765
Lys Pro Gly Ser Gly Glu Gly Ser Thr Lys Gly Gln Val Gln Leu Gln
            770                 775                 780
Gln Ser Gly Ala Glu Leu Val Arg Pro Gly Ser Ser Val Lys Ile Ser
785                 790                 795                 800
Cys Lys Ala Ser Gly Tyr Ala Phe Ser Ser Tyr Trp Met Asn Trp Val
                805                 810                 815
Lys Gln Arg Pro Gly Gln Gly Leu Glu Trp Ile Gly Gln Ile Trp Pro
            820                 825                 830
Gly Asp Gly Asp Thr Asn Tyr Asn Gly Lys Phe Lys Gly Lys Ala Thr
            835                 840                 845
Leu Thr Ala Asp Glu Ser Ser Ser Thr Ala Tyr Met Gln Leu Ser Ser
            850                 855                 860
Leu Ala Ser Glu Asp Ser Ala Val Tyr Phe Cys Ala Arg Arg Glu Thr
865                 870                 875                 880
Thr Thr Val Gly Arg Tyr Tyr Tyr Ala Met Asp Tyr Trp Gly Gln Gly
                885                 890                 895
Thr Ser Val Thr Val Ser Ser
                900

<210> SEQ ID NO 8
```

<211> LENGTH: 581
<212> TYPE: PRT
<213> ORGANISM: Artificial
<220> FEATURE:
<223> OTHER INFORMATION: Polypeptide

<400> SEQUENCE: 8

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Asn Val Leu Ala Leu Lys Val
            85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Ser Arg Phe Gly
            115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Ala Gly Gln Asp
            165                 170                 175

Ala Met Tyr Glu Tyr Met Ala Ser Ala Cys Ala Gly Asn Arg Val Arg
            180                 185                 190

Arg Ser Val Gly Ser Ser Leu Ser Cys Ile Asn Leu Asp Trp Asp Val
            195                 200                 205

Ile Arg Asp Lys Thr Lys Thr Lys Ile Glu Ser Leu Lys Glu His Gly
    210                 215                 220

Pro Ile Ser Asn Lys Met Ser Glu Ser Pro Asn Lys Thr Val Ser Glu
225                 230                 235                 240

Glu Lys Ala Lys Ser Tyr Leu Glu Glu Phe His Gln Thr Ala Leu Glu
            245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
            275                 280                 285

Ile Asp Ser Ser Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
            325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
            355                 360                 365

Gln Val Val His Asn Ser Tyr Asn Arg Pro Ala Tyr Ser Pro Gly His
    370                 375                 380

-continued

Gly Thr Gln Pro Phe Glu Ala Ser Gly Gly Pro Glu Asn Ser Asp Ser
385                 390                 395                 400

Glu Cys Pro Leu Ser His Asp Gly Tyr Cys Leu His Asp Gly Val Cys
            405                 410                 415

Met Tyr Ile Glu Ala Leu Asp Lys Tyr Ala Cys Asn Cys Val Val Gly
        420                 425                 430

Tyr Ile Gly Glu Arg Cys Gln Tyr Arg Asp Leu Lys Trp Trp Glu Leu
    435                 440                 445

Arg Pro Ser Gly Gln Ala Gly Ala Ala Ser Glu Ser Leu Phe Val
450                 455                 460

Ser Asn His Ala Tyr Gly Pro Val Pro Ser Thr Ala Leu Arg Glu
465                 470                 475                 480

Leu Ile Glu Glu Leu Val Asn Ile Thr Gln Asn Gln Lys Ala Pro Leu
                485                 490                 495

Cys Asn Gly Ser Met Val Trp Ser Ile Asn Leu Thr Ala Gly Met Tyr
            500                 505                 510

Cys Ala Ala Leu Glu Ser Leu Ile Asn Val Ser Gly Cys Ser Ala Ile
        515                 520                 525

Glu Lys Thr Gln Arg Met Leu Ser Gly Phe Cys Pro His Lys Val Ser
530                 535                 540

Ala Gly Gln Phe Ser Ser Leu His Val Arg Asp Thr Lys Ile Glu Val
545                 550                 555                 560

Ala Gln Phe Val Lys Asp Leu Leu His Leu Lys Lys Leu Phe Arg
                565                 570                 575

Glu Gly Arg Phe Asn
            580

<210> SEQ ID NO 9
<211> LENGTH: 905
<212> TYPE: PRT
<213> ORGANISM: Artificial
<220> FEATURE:
<223> OTHER INFORMATION: Polypeptide

<400> SEQUENCE: 9

Gly Ala Asp Asp Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Lys Ala Gly Val Val
65                  70                  75                  80

Val Lys Val Thr Tyr Pro Gly Leu Thr Asn Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Ser Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

```
Val Glu Leu Glu Ile Asn Phe Glu Thr Arg Gly Lys Ala Gly Gln Asp
                165                 170                 175

Ala Met Tyr Glu Tyr Met Ala Ser Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Ser Asn Lys Met Ser Glu Ser Pro Asn Lys Thr Val Ser Glu
225                 230                 235                 240

Glu Lys Ala Lys Ser Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Ser Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Gly Thr Gln Pro Phe Glu Ala Ser Gly Gly Pro Glu Asp Ile Gln Met
385                 390                 395                 400

Thr Gln Ser Pro Ser Ser Leu Ser Ala Ser Val Gly Asp Arg Val Thr
                405                 410                 415

Ile Thr Cys Arg Ser Thr Lys Ser Leu Leu His Ser Asn Gly Ile Thr
            420                 425                 430

Tyr Leu Tyr Trp Tyr Gln Gln Lys Pro Gly Lys Ala Pro Lys Leu Leu
        435                 440                 445

Ile Tyr Gln Met Ser Asn Leu Ala Ser Gly Val Pro Ser Arg Phe Ser
    450                 455                 460

Ser Ser Gly Ser Gly Thr Asp Phe Thr Leu Thr Ile Ser Ser Leu Gln
465                 470                 475                 480

Pro Glu Asp Phe Ala Thr Tyr Tyr Cys Ala Gln Asn Leu Glu Ile Pro
                485                 490                 495

Arg Thr Phe Gly Gln Gly Thr Lys Val Glu Leu Lys Arg Ala Thr Pro
            500                 505                 510

Ser His Asn Ser His Gln Val Pro Ser Ala Gly Gly Pro Thr Ala Asn
        515                 520                 525

Ser Gly Thr Ser Gly Glu Val Gln Leu Val Gln Ser Gly Pro Gly Leu
530                 535                 540

Val Gln Pro Gly Gly Ser Val Arg Ile Ser Cys Ala Ala Ser Gly Tyr
545                 550                 555                 560

Thr Phe Thr Asn Tyr Gly Met Asn Trp Val Lys Gln Ala Pro Gly Lys
                565                 570                 575
```

```
Gly Leu Glu Trp Met Gly Trp Ile Asn Thr Tyr Thr Gly Glu Ser Thr
            580                 585                 590

Tyr Ala Asp Ser Phe Lys Gly Arg Phe Thr Phe Ser Leu Asp Thr Ser
        595                 600                 605

Ala Ser Ala Ala Tyr Leu Gln Ile Asn Ser Leu Arg Ala Glu Asp Thr
    610                 615                 620

Ala Val Tyr Tyr Cys Ala Arg Phe Ala Ile Lys Gly Asp Tyr Trp Gly
625                 630                 635                 640

Gln Gly Thr Leu Leu Thr Val Ser Ser Pro Ser Gly Gln Ala Gly Ala
                645                 650                 655

Ala Ala Ser Glu Ser Leu Phe Val Ser Asn His Ala Tyr Asp Val Gln
            660                 665                 670

Leu Thr Gln Ser Pro Ala Ile Leu Ser Ala Ser Pro Gly Glu Lys Val
        675                 680                 685

Thr Met Thr Cys Arg Ala Thr Pro Ser Val Ser Tyr Met His Trp Tyr
    690                 695                 700

Gln Gln Lys Pro Gly Ser Ser Pro Lys Pro Trp Ile Tyr Thr Thr Ser
705                 710                 715                 720

Asn Leu Ala Ser Gly Val Pro Ala Arg Phe Ser Gly Gly Ser Gly
                725                 730                 735

Thr Ser Tyr Ser Leu Thr Val Ser Arg Val Glu Ala Glu Asp Ala Ala
            740                 745                 750

Thr Tyr Tyr Cys Gln Gln Trp Ser Arg Ser Pro Pro Thr Phe Gly Gly
        755                 760                 765

Gly Ser Lys Leu Glu Ile Lys Gly Ser Thr Ser Gly Ser Gly Lys Ser
    770                 775                 780

Ser Glu Gly Lys Gly Val Gln Leu Gln Glu Ser Gly Pro Glu Val Val
785                 790                 795                 800

Lys Pro Gly Gly Ser Met Lys Ile Ser Cys Lys Thr Ser Gly Tyr Ser
                805                 810                 815

Phe Thr Gly His Thr Met Asn Trp Val Lys Gln Ser His Gly Lys Asn
            820                 825                 830

Leu Glu Trp Ile Gly Leu Ile Asn Pro Tyr Asn Gly Asp Thr Asn Tyr
        835                 840                 845

Asn Gln Lys Phe Lys Gly Lys Ala Thr Phe Thr Val Asp Lys Ser Ser
    850                 855                 860

Ser Thr Ala Tyr Met Glu Leu Leu Ser Leu Thr Ser Glu Asp Ser Ala
865                 870                 875                 880

Val Tyr Tyr Cys Ala Arg Arg Val Thr Asp Trp Tyr Phe Asp Val Trp
                885                 890                 895

Gly Ala Gly Thr Thr Val Thr Val Ser
            900                 905

<210> SEQ ID NO 10
<211> LENGTH: 916
<212> TYPE: PRT
<213> ORGANISM: Artificial
<220> FEATURE:
<223> OTHER INFORMATION: Polypeptide

<400> SEQUENCE: 10

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30
```

```
Lys Gly Ile Gln Lys Pro Lys Ser Gly Thr Gln Gly Asn Tyr Asp Asp
            35                  40                  45

Asp Trp Lys Gly Phe Tyr Ser Thr Asp Asn Lys Tyr Asp Ala Ala Gly
 50                  55                  60

Tyr Ser Val Asp Asn Glu Asn Pro Leu Ser Gly Lys Ala Gly Gly Val
 65                  70                  75                  80

Val Lys Val Thr Tyr Pro Gly Leu Thr Asn Val Leu Ala Leu Lys Val
                 85                  90                  95

Asp Asn Ala Glu Thr Ile Lys Lys Glu Leu Gly Leu Ser Leu Thr Glu
                100                 105                 110

Pro Leu Met Glu Gln Val Gly Thr Glu Phe Ile Ser Arg Phe Gly
                115                 120                 125

Asp Gly Ala Ser Arg Val Val Leu Ser Leu Pro Phe Ala Glu Gly Ser
        130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Ala Gly Gln Asp
                165                 170                 175

Ala Met Tyr Glu Tyr Met Ala Ser Ala Cys Ala Gly Asn Arg Val Arg
                180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
        210                 215                 220

Pro Ile Ser Asn Lys Met Ser Glu Ser Pro Asn Lys Thr Val Ser Glu
225                 230                 235                 240

Glu Lys Ala Lys Ser Tyr Leu Glu Glu Phe His Gln Thr Ala Leu Glu
                245                 250                 255

His Pro Glu Leu Ser Glu Leu Lys Thr Val Thr Gly Thr Asn Pro Val
                260                 265                 270

Phe Ala Gly Ala Asn Tyr Ala Ala Trp Ala Val Asn Val Ala Gln Val
        275                 280                 285

Ile Asp Ser Ser Thr Ala Asp Asn Leu Glu Lys Thr Thr Ala Ala Leu
        290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
                340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
        370                 375                 380

Gly Thr Gln Pro Phe Glu Ala Ser Gly Gly Pro Glu Asp Ile Gln Met
385                 390                 395                 400

Thr Gln Ser Pro Ser Ser Leu Ser Ala Ser Val Gly Asp Arg Val Thr
                405                 410                 415

Ile Thr Cys Arg Ser Thr Lys Ser Leu Leu His Ser Asn Gly Ile Thr
                420                 425                 430

Tyr Leu Tyr Trp Tyr Gln Gln Lys Pro Gly Lys Ala Pro Lys Leu Leu
        435                 440                 445

Ile Tyr Gln Met Ser Asn Leu Ala Ser Gly Val Pro Ser Arg Phe Ser
```

```
                450             455             460
Ser Ser Gly Ser Gly Thr Asp Phe Thr Leu Thr Ile Ser Ser Leu Gln
465                 470                 475                 480

Pro Glu Asp Phe Ala Thr Tyr Tyr Cys Ala Gln Asn Leu Glu Ile Pro
                485                 490                 495

Arg Thr Phe Gly Gln Gly Thr Lys Val Glu Leu Lys Arg Ala Thr Pro
                500                 505                 510

Ser His Asn Ser His Gln Val Pro Ser Ala Gly Gly Pro Thr Ala Asn
515                 520                 525

Ser Gly Thr Ser Gly Glu Val Gln Leu Val Gln Ser Gly Pro Gly Leu
        530                 535                 540

Val Gln Pro Gly Gly Ser Val Arg Ile Ser Cys Ala Ala Ser Gly Tyr
545                 550                 555                 560

Thr Phe Thr Asn Tyr Gly Met Asn Trp Val Lys Gln Ala Pro Gly Lys
                565                 570                 575

Gly Leu Glu Trp Met Gly Trp Ile Asn Thr Tyr Thr Gly Glu Ser Thr
                580                 585                 590

Tyr Ala Asp Ser Phe Lys Gly Arg Phe Thr Phe Ser Leu Asp Thr Ser
                595                 600                 605

Ala Ser Ala Ala Tyr Leu Gln Ile Asn Ser Leu Arg Ala Glu Asp Thr
                610                 615                 620

Ala Val Tyr Tyr Cys Ala Arg Phe Ala Ile Lys Gly Asp Tyr Trp Gly
625                 630                 635                 640

Gln Gly Thr Leu Leu Thr Val Ser Ser Glu Pro Lys Ser Ser Asp Lys
                645                 650                 655

Thr His Thr Ser Pro Pro Ser Pro Asp Ile Val Leu Ser Gln Ser Pro
                660                 665                 670

Ala Ile Met Ser Ala Ser Pro Gly Glu Lys Val Thr Ile Ser Cys Ser
                675                 680                 685

Ala Ser Ser Ser Val Ser Tyr Met Tyr Trp Tyr Gln Gln Lys Pro Gly
690                 695                 700

Ser Ser Pro Lys Pro Trp Ile Tyr Arg Thr Ser Asn Leu Ala Ser Gly
705                 710                 715                 720

Val Pro Ala Arg Phe Ser Gly Ser Gly Ser Gly Thr Ser Tyr Ser Leu
                725                 730                 735

Thr Ile Ser Ser Met Glu Ala Glu Asp Ala Ala Thr Tyr Tyr Cys Gln
                740                 745                 750

Gln Tyr His Ser Tyr Pro Pro Thr Phe Gly Ala Gly Thr Lys Leu Glu
                755                 760                 765

Leu Lys Ser Ser Gly Gly Gly Ser Gly Gly Gly Gly Ser
770                 775                 780

Ser Arg Ser Ser Leu Glu Val Lys Leu Val Glu Ser Gly Pro Glu Leu
785                 790                 795                 800

Lys Lys Pro Gly Glu Thr Val Lys Ile Ser Cys Lys Ala Ser Gly Tyr
                805                 810                 815

Thr Phe Thr Asp Tyr Ser Met His Trp Val Asn Gln Ala Pro Gly Lys
                820                 825                 830

Gly Leu Lys Trp Met Gly Trp Ile Asn Thr Glu Thr Gly Glu Pro Ser
                835                 840                 845

Tyr Ala Asp Asp Phe Lys Gly Arg Phe Ala Phe Ser Leu Glu Thr Ser
                850                 855                 860

Ala Ser Thr Ala Tyr Leu Gln Ile Asn Asn Leu Lys Asn Glu Asp Thr
865                 870                 875                 880
```

```
Ala Thr Tyr Phe Cys Ala Thr Asp Tyr Gly Asp Tyr Phe Asp Tyr Trp
                885                 890                 895

Gly Gln Gly Thr Thr Leu Thr Val Ser Ser Ala Lys Thr Thr Pro Pro
        900                 905                 910

Ser Val Thr Ser
        915

<210> SEQ ID NO 11
<211> LENGTH: 604
<212> TYPE: PRT
<213> ORGANISM: Artificial
<220> FEATURE:
<223> OTHER INFORMATION: Polypeptide

<400> SEQUENCE: 11

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Asn Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Ser Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Ala Gly Gln Asp
                165                 170                 175

Ala Met Tyr Glu Tyr Met Ala Ser Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Ser Asn Lys Met Ser Glu Ser Pro Asn Lys Thr Val Ser Glu
225                 230                 235                 240

Glu Lys Ala Lys Ser Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Ser Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320
```

Val His His Asn Thr Glu Glu Ile Val Ala Gln Ser Ile Ala Leu Ser
              325                 330                 335

Ser Leu Met Val Ala Gln Ala Ile Pro Leu Val Gly Glu Leu Val Asp
          340                 345                 350

Ile Gly Phe Ala Ala Tyr Asn Phe Val Glu Ser Ile Ile Asn Leu Phe
              355                 360                 365

Gln Val Val His Asn Ser Tyr Asn Arg Pro Ala Tyr Ser Pro Gly His
    370                 375                 380

Gly Thr Gln Pro Phe Glu Ala Ser Gly Gly Pro Glu Asn Ser Asp Ser
385                 390                 395                 400

Glu Cys Pro Leu Ser His Asp Gly Tyr Cys Leu His Asp Gly Val Cys
              405                 410                 415

Met Tyr Ile Glu Ala Leu Asp Lys Tyr Ala Cys Asn Cys Val Val Gly
              420                 425                 430

Tyr Ile Gly Glu Arg Cys Gln Tyr Arg Asp Leu Lys Trp Trp Glu Leu
              435                 440                 445

Arg Pro Ser Gly Gln Ala Gly Ala Ala Ser Glu Ser Leu Phe Val
    450                 455                 460

Ser Asn His Ala Tyr Ser Asn Glu Leu His Gln Val Pro Ser Asn Cys
465                 470                 475                 480

Asp Cys Leu Asn Gly Gly Thr Cys Val Ser Asn Lys Tyr Phe Ser Asn
              485                 490                 495

Ile His Trp Cys Asn Cys Pro Lys Lys Phe Gly Gly Gln His Cys Glu
              500                 505                 510

Ile Asp Lys Ser Lys Thr Cys Tyr Glu Gly Asn Gly His Phe Tyr Arg
              515                 520                 525

Gly Lys Ala Ser Thr Asp Thr Met Gly Arg Pro Cys Leu Pro Trp Asn
              530                 535                 540

Ser Ala Thr Val Leu Gln Gln Thr Tyr His Ala His Arg Ser Asp Ala
545                 550                 555                 560

Leu Gln Leu Gly Leu Gly Lys His Asn Tyr Cys Arg Asn Pro Asp Asn
              565                 570                 575

Arg Arg Arg Pro Trp Cys Tyr Val Gln Val Gly Leu Lys Pro Leu Val
              580                 585                 590

Gln Glu Cys Met Val His Asp Cys Ala Asp Gly Lys
    595                 600

<210> SEQ ID NO 12
<211> LENGTH: 790
<212> TYPE: PRT
<213> ORGANISM: Artificial
<220> FEATURE:
<223> OTHER INFORMATION: Polypeptide

<400> SEQUENCE: 12

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
              20                  25                  30

Lys Gly Ile Gln Lys Pro Lys Ser Gly Thr Gln Gly Asn Tyr Asp Asp
          35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

```
Val Lys Val Thr Tyr Pro Gly Leu Thr Asn Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Phe Ile Ser Arg Phe Gly
        115                 120                 125

Asp Gly Ala Ser Arg Val Val Leu Ser Leu Pro Phe Ala Glu Gly Ser
130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Ala Gly Gln Asp
                165                 170                 175

Ala Met Tyr Glu Tyr Met Ala Ser Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Ser Asn Lys Met Ser Glu Ser Pro Asn Lys Thr Val Ser Glu
225                 230                 235                 240

Glu Lys Ala Lys Ser Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Ser Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Gly Thr Gln Pro Phe Glu Ala Ser Gly Gly Pro Glu Gln Val Gln Leu
385                 390                 395                 400

Gln Gln Ser Gly Ala Glu Leu Val Arg Pro Gly Ala Ser Val Thr Leu
                405                 410                 415

Ser Cys Lys Ala Ser Gly Tyr Thr Phe Ser Asp Tyr Glu Met His Trp
            420                 425                 430

Val Ile Gln Thr Pro Val His Gly Leu Glu Trp Ile Gly Ala Ile Asp
        435                 440                 445

Pro Glu Thr Gly Gly Thr Ala Tyr Asn Gln Lys Phe Lys Gly Lys Ala
    450                 455                 460

Ile Leu Thr Ala Asp Lys Ser Ser Ser Thr Ala Tyr Met Glu Leu Arg
465                 470                 475                 480

Ser Leu Thr Ser Glu Asp Ser Ala Val Tyr Tyr Cys Thr Gly Tyr Tyr
                485                 490                 495
```

```
Asp Tyr Asp Ser Phe Thr Tyr Trp Gly Gln Gly Thr Leu Val Thr Val
                500                 505                 510

Ser Ala Gly Gly Gly Gly Ser Gly Gly Gly Ser Gly Gly Gly Gly
            515                 520                 525

Ser Asp Ile Val Met Thr Gln Ser Gln Lys Ile Met Ser Thr Thr Val
        530                 535                 540

Gly Asp Arg Val Ser Ile Thr Cys Lys Ala Ser Gln Asn Val Asp Ala
545                 550                 555                 560

Ala Val Ala Trp Tyr Gln Gln Lys Pro Gly Gln Ser Pro Lys Leu Leu
                565                 570                 575

Ile Tyr Ser Ala Ser Asn Arg Tyr Thr Gly Val Pro Asp Arg Phe Thr
                580                 585                 590

Gly Ser Gly Ser Gly Thr Asp Phe Thr Leu Thr Ile Ser Asn Met Gln
            595                 600                 605

Ser Glu Asp Leu Ala Asp Tyr Phe Cys Gln Gln Tyr Asp Ile Tyr Pro
        610                 615                 620

Tyr Thr Phe Gly Gly Gly Thr Lys Leu Glu Ile Lys Pro Ser Gly Gln
625                 630                 635                 640

Ala Gly Ala Ala Ala Ser Glu Ser Leu Phe Val Ser Asn His Ala Tyr
                645                 650                 655

Ser Asn Glu Leu His Gln Val Pro Ser Asn Cys Asp Cys Leu Asn Gly
                660                 665                 670

Gly Thr Cys Val Ser Asn Lys Tyr Phe Ser Asn Ile His Trp Cys Asn
            675                 680                 685

Cys Pro Lys Lys Phe Gly Gly Gln His Cys Glu Ile Asp Lys Ser Lys
        690                 695                 700

Thr Cys Tyr Glu Gly Asn Gly His Phe Tyr Arg Gly Lys Ala Ser Thr
705                 710                 715                 720

Asp Thr Met Gly Arg Pro Cys Leu Pro Trp Ser Ala Thr Val Leu Gln
                725                 730                 735

Gln Thr Tyr His Ala His Arg Ser Asp Ala Leu Gln Leu Gly Leu Gly
                740                 745                 750

Lys His Asn Tyr Cys Arg Asn Pro Asp Asn Arg Arg Pro Trp Cys
            755                 760                 765

Tyr Val Gln Val Gly Leu Lys Pro Leu Val Gln Glu Cys Met Val His
770                 775                 780

Asp Cys Ala Asp Gly Lys
785                 790

<210> SEQ ID NO 13
<211> LENGTH: 1743
<212> TYPE: DNA
<213> ORGANISM: Artificial
<220> FEATURE:
<223> OTHER INFORMATION: Polynucleotide

<400> SEQUENCE: 13
ggcgctgatg atgttgttga ttcttctaaa tcttttgtga tggaaaactt ttcttcgtac      60
cacgggacta aacctggtta tgtagattcc attcaaaaag gtatacaaaa gccaaaatct     120
ggtacacaag gaattatga cgatgattgg aagggtttt atagtaccga caataaatac      180
gacgctgcgg gatactctgt agataatgaa aacccgctct ctggaaaagc tggaggcgtg     240
gtcaaagtga cgtatccagg actgacgaac gttctcgcac taaaagtgga taatgccgaa     300
actattaaga aagagttagg tttaagtctc actgaaccgt tgatggagca agtcggaacg     360
```

-continued

```
gaagagttta tctcaaggtt cggtgatggt gcttcgcgtg tagtgctcag ccttcccttc    420
gctgagggga gttctagcgt tgaatatatt aataactggg aacaggcgaa agcgttaagc    480
gtagaacttg agattaattt tgaaacccgt ggaaaagctg gccaagatgc gatgtatgag    540
tatatggctt cagcctgtgc aggaaatcgt gtcaggcgat cagtaggtag ctcattgtca    600
tgcataaatc ttgattggga tgtcataagg gataaaacta agacaaagat agagtctttg    660
aaagagcatg gccctatctc aaataaaatg agcgaaagtc ccaataaaac agtatctgag    720
gaaaaagcta aatcatacct agaagaattt catcaaacgg cattagagca tcctgaattg    780
tcagaactta aaaccgttac tgggaccaat cctgtattcg ctggggctaa ctatgcggcg    840
tgggcagtaa acgttgcgca agttatcgat agctcaacag ctgataattt ggaaaagaca    900
actgctgctc tttcgatact tcctggtatc ggtagcgtaa tgggcattgc agacggtgcc    960
gttcaccaca atacagaaga gatagtggca caatcaatag ctttatcgtc tttaatggtt   1020
gctcaagcta ttccattggt aggagagcta gttgatattg gtttcgctgc atataatttt   1080
gtagagagta ttatcaattt atttcaagta gttcataatt cgtataatcg tcccgcgtat   1140
tctccggggc atggaacgca accatttgaa gcttccggag gtcccgagaa cagcgacagc   1200
gaatgtccgc tgagccacga cggttactgt ctgcacgacg gtgtttgtat gtacatcgaa   1260
gctctagaca aatacgcttg taactgtgtt gttggttaca tcggtgaacg ctgtcagtac   1320
cgcgacctga aatggtggga actgcgcccg tctggtcagg ctggtgctgc tgctagcgaa   1380
tctctgttcg tttctaacca cgcttacggc cctgtgcctc cctctacagc cctcagggag   1440
ctcattgagg agctggtcaa catcacccag aaccagaagg ctccgctctg caatggcagc   1500
atggtatgga gcatcaacct gacagctggc atgtactgtg cagccctgga atccctgatc   1560
aacgtgtcag gctgcagtgc catcgagaag acccagagga tgctgagcgg attctgcccg   1620
cacaaggtct cagctgggca gttttccagc ttgcatgtcc gagacaccaa aatcgaggtg   1680
gcccagtttg taaaggacct gctcttacat ttaaagaaac ttttttcgcga gggacggttc   1740 aac                                                                 1743
```